US007795483B2

(12) United States Patent
Kulprathipanja et al.

(10) Patent No.: US 7,795,483 B2
(45) Date of Patent: Sep. 14, 2010

(54) PHENYL-ALKANE COMPOSITIONS PRODUCED USING AN ADSORPTIVE SEPARATION SECTION

(75) Inventors: Santi Kulprathipanja, Inverness, IL (US); Richard E. Marinangeli, Arlington Heights, IL (US); Stephen W. Sohn, Arlington Heights, IL (US); Thomas R. Fritsch, Tucson, AZ (US); R. Joe Lawson, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 1329 days.

(21) Appl. No.: 10/658,703

(22) Filed: Sep. 9, 2003

(65) Prior Publication Data

US 2004/0116756 A1   Jun. 17, 2004

Related U.S. Application Data

(63) Continuation-in-part of application No. 09/650,886, filed on Aug. 29, 2000, now Pat. No. 6,617,481, which is a continuation-in-part of application No. 09/222,423, filed on Dec. 29, 1998, now Pat. No. 6,252,127.

(51) Int. Cl.
  *C07C 13/00* (2006.01)
  *C07C 15/00* (2006.01)
(52) U.S. Cl. .......................... 585/24; 585/323; 585/324; 585/449; 585/455; 585/661; 585/740; 585/750; 585/826; 562/93
(58) Field of Classification Search ............ 562/93; 585/323, 324, 449, 455, 661, 740, 750, 826, 585/24
See application file for complete search history.

(56) References Cited

U.S. PATENT DOCUMENTS 2,477,382 A   7/1949   Lewis ....................... 260/671
(Continued)

FOREIGN PATENT DOCUMENTS

WO   WO 99/05082   2/1999
(Continued)

OTHER PUBLICATIONS

Vora, B.V. et al. "Latest LAB Developments" *Hydrocarbon Processing* Nov. 1984 pp. 86-90.
(Continued)

*Primary Examiner*—Glenn Caldarola
*Assistant Examiner*—Prem C. Singh
(74) *Attorney, Agent, or Firm*—Arthur E Gooding

(57) ABSTRACT

The present invention is a process for producing phenyl-alkanes by paraffin adsorptive separation followed by paraffin dehydrogenation and then by alkylation of a phenyl compound by a lightly branched olefin. The adsorptive separation step employs a silicalite adsorbent and, as the desorbent, a $C_5$-$C_8$ linear paraffin, a $C_5$-$C_8$ cycloparaffin, a branched paraffin such as isooctane, or mixtures thereof. The effluent of the alkylation zone comprises paraffins that are recycled to the adsorptive separation step or to the dehydrogenation step. This invention is also a process that that sulfonates phenyl-alkanes having lightly branched aliphatic alkyl groups that to produce modified alkylbenzene sulfonates. In addition, this invention is the compositions produced by these processes, which can be used as detergents having improved cleaning effectiveness in hard and/or cold water while also having biodegradability comparable to that of linear alkylbenzene sulfonates, as lubricants, and as lubricant additives. This invention is moreover the use of compositions produced by these processes as lubricants and lubricant additives.

23 Claims, 2 Drawing Sheets

U.S. PATENT DOCUMENTS

| | | | | |
|---|---|---|---|---|
| 3,303,233 | A | * | 2/1967 | Jones .................... 585/324 |
| 3,355,484 | A | | 11/1967 | Bloch .................... 562/94 |
| 3,413,373 | A | | 11/1968 | Bloch .................... 585/315 |
| 3,910,994 | A | | 10/1975 | Bloch et al. .................... 562/93 |
| 4,235,810 | A | | 11/1980 | Osselet et al. .................... 562/94 |
| 4,301,316 | A | | 11/1981 | Young .................... 585/455 |
| 4,301,317 | A | | 11/1981 | Young .................... 585/455 |
| 4,329,280 | A | | 5/1982 | Cleary et al. .................... 530/207 |
| 4,367,364 | A | | 1/1983 | Kulprathipanja et al. .... 585/826 |
| 4,455,444 | A | | 6/1984 | Kulprathipanja et al. .... 585/826 |
| 4,455,445 | A | | 6/1984 | Neuzil et al. .................... 585/820 |
| 4,956,521 | A | | 9/1990 | Volles .................... 585/826 |
| 4,959,491 | A | | 9/1990 | Threlkel .................... 562/94 |
| 4,982,052 | A | | 1/1991 | Nolte .................... 585/822 |
| 5,055,633 | A | | 10/1991 | Volles .................... 585/826 |
| 5,055,634 | A | | 10/1991 | Volles .................... 585/826 |
| 5,132,486 | A | | 7/1992 | Wylie .................... 585/826 |
| 5,196,574 | A | | 3/1993 | Kocal .................... 562/94 |
| 5,196,624 | A | | 3/1993 | Threlkel et al. .................... 585/513 |
| 5,196,625 | A | | 3/1993 | Threlkel et al. .................... 585/513 |
| 5,262,144 | A | | 11/1993 | McCulloch .................... 423/328.2 |
| 5,276,231 | A | | 1/1994 | Kocal et al. .................... 585/323 |
| 5,276,246 | A | | 1/1994 | McCulloch et al. .................... 585/829 |
| 5,292,990 | A | | 3/1994 | Kantner et al. .................... 585/820 |
| 5,302,732 | A | | 4/1994 | Steigleder et al. .................... 554/98 |
| 5,344,997 | A | | 9/1994 | Kocal .................... 568/628 |
| 5,491,271 | A | | 2/1996 | Marinangeli et al. .................... 585/468 |
| 6,069,285 | A | * | 5/2000 | Fritsch et al. .................... 585/449 |
| 6,069,289 | A | | 5/2000 | Dandekar et al. .................... 585/820 |
| 6,111,158 | A | | 8/2000 | Marinangeli et al. .................... 585/467 |
| 6,187,981 | B1 | | 2/2001 | Marinangeli et al. .................... 585/323 |
| 6,225,516 | B1 | | 5/2001 | Radici et al. .................... 585/323 |
| 6,515,169 | B1 | * | 2/2003 | Marinangeli et al. .......... 562/93 |
| 6,589,927 | B1 | | 7/2003 | Kott et al. .................... 510/357 |

FOREIGN PATENT DOCUMENTS

| | | |
|---|---|---|
| WO | WO 99/05084 | 2/1999 |
| WO | WO 99/05241 | 2/1999 |
| WO | WO 99/05243 | 2/1999 |
| WO | WO 99/07656 | 2/1999 |

OTHER PUBLICATIONS

Schulz, R.C. et al. "LAB Production" Poster Session at $2^{nd}$ World Conference on Detergents Montreux, Switzerland; Oct. 5-10, 1986.

Hoering, Thomas C. et al. "Shape-Selective Sorption of Monomethylalkanes by Silicate, a Zeolitic Form of Silica," *Journal of Chromatography*, 316 (1984) pp. 333-341.

"Lubrication and Lubricants" in *Kirk-Othmer Encyclopedia of Chemical Technology*, $4^{th}$ Ed., vol. 15 (John Wiley and Sons, New York, 1995) pp. 463-515. ISBN 0-471-52684-3 (v.15) TP9.E685 1992.

Watson, Roger W. et al. *Additives—The Right Stuff for Automotive Engine Oils* Fuels and Lubricants Technology: An Overview SP-603 Copyright 1984 Society of Automotive Engineers, Inc. ISBN 0-89883-825-8 SAE/SP-84/603 pp. 17-28.

Smalheer, C.V. et al. *Chemistry of Additives* Lubricant Additives pp. 17-28 1967 The Lubrizol Corporation, Cleveland, Ohio Library of Congress Catalogue Card No. 67-19868.

*Handbook of Petroleum Refining Processes* edited by Robert A. Meyers, (McGraw-Hill, New York, $2^{nd}$ Ed., 1997), pp. 1.53 to 1.66 and pp. 5.11 to 5.19.

* cited by examiner

PHENYL-ALKANE COMPOSITIONS PRODUCED USING AN ADSORPTIVE SEPARATION SECTION

CROSS-REFERENCE TO RELATED APPLICATIONS

This application is a continuation-in-part of U.S. application Ser. No. 09/650,886, filed Aug. 29, 2000, the entire contents of which are hereby incorporated herein by reference, which is a continuation-in-part of U.S. application Ser. No. 09/222,423, filed Dec. 29, 1998, now issued as U.S. Pat. No. 6,252,127, the entire contents of which are hereby incorporated herein by reference.

FIELD OF THE INVENTION

The invention relates to a process for the selective production of phenyl-alkane and phenyl-alkane sulfonate compositions, to the particular phenyl-alkane are phenyl-alkane sulfonate compositions produced therefrom, and to uses of those compositions.

BACKGROUND OF THE INVENTION

More than thirty years ago, many household laundry detergents were made of branched alkylbenzene sulfonates (BABS). BABS are manufactured from a type of alkylbenzenes called branched alkylbenzenes (BAB).

Alkylbenzenes (phenyl-alkanes) refers to a general category of compounds having an aliphatic alkyl group bound to a phenyl group and having the general formula of $(m_i\text{-alkyl}_i)_i$-n-phenyl-alkane. The aliphatic alkyl group consists of an aliphatic alkyl chain, which is referred to by "alkane" in the $(m_i\text{-alkyl}_i)_i$-n-phenyl-alkane formula. Of the chains of the aliphatic alkyl group, the aliphatic alkyl chain is the longest straight chain that has a carbon bound to the phenyl group. The aliphatic alkyl group may also consist of one or more alkyl group branches, each of which is attached to the aliphatic alkyl chain and is designated by a corresponding "$(m_i\text{-alkyl}_i)_i$" in the $(m_i\text{-alkyl}_i)_i$-n-phenyl-alkane formula. If it is possible to select two or more chains of equal lengths as the aliphatic alkyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $m_i$ of the aliphatic alkyl chain. The phenyl group is attached to the aliphatic alkyl group, specifically to carbon number n of the aliphatic alkyl chain. The aliphatic alkylation chain is numbered from one end to the other, the direction being chosen so as to give the lowest number possible to the position of the phenyl group.

The standard process used by the petrochemical industry for producing BAB consists of oligomerizing light olefins, particularly propylene, to branched olefins having 10 to 14 carbon atoms and then alkylating benzene with the branched olefins in the presence of a catalyst such as HF. Although the product BAB comprises a large number of alkyl-phenyl-alkanes having the general formula $(m_i\text{-alkyl}_i)_i$-n-phenyl-alkane, two examples of BAB are m-alkyl-m-alkyl-n-phenyl-alkanes where m≠n, and m-alkyl-m-phenyl-alkanes where m≧2.

The most prominent common characteristic of BAB is that, for a large proportion of BAB, there is attached to the aliphatic alkyl chain of BAB generally at least one alkyl group branch, and more commonly three or more alkyl group branches. BAB thus has a relatively large number of primary carbon atoms per aliphatic alkyl group, since the number of primary carbon atoms per aliphatic alkyl group in BAB equals the number of alkyl group branches per aliphatic alkyl group plus either one if n=1, or two if n≧2, provided that the alkyl group branches themselves are unbranched. If any alkyl group branch itself is branched, then the aliphatic alkyl group in BAB has even more primary carbon atoms. Thus the aliphatic alkyl group in BAB usually has three, four, or more primary carbon atoms. As for the alkyl group branches of the aliphatic alkyl group in BAB, each alkyl group branch is usually a methyl group branch, although ethyl, propyl, or higher alkyl group branches are possible.

Another typical characteristic of BAB is that the phenyl group in BAB can be attached to any non-primary carbon atom of the aliphatic alkyl chain. Except for 1-phenyl-alkanes whose formation is known to be disfavored due to the relative instability of the primary carbenium ion and neglecting the relatively minor effect of the branches of the branched paraffins, the oligomerization step produces a carbon-carbon double bond that is randomly distributed along the length of the aliphatic alkenyl chain, and the alkylation step nearly randomly attaches the phenyl group to a carbon along the aliphatic alkyl chain. Thus, for example, a BAB that has an aliphatic alkyl chain having 10 carbon atoms would be expected to be an approximately random distribution of 2-, 3-, 4-, and 5-phenyl-alkanes, and the selectivity to 2-phenyl alkane would be 25 if the distribution was perfectly random, but is typically between about 10 and about 40. U.S. Pat. No. 5,196,625 discloses a dimerization step which produces olefins having a carbon-carbon double bond between the third and fourth, between the fourth and fifth, and between the sixth and seventh carbon atoms of the aliphatic alkenyl chain.

A third common characteristic of BAB is that one of the carbons of the aliphatic alkyl group is a quaternary carbon. The quaternary carbon may, or may not, be the carbon in the aliphatic alkyl group that is bonded by a carbon-carbon bond to a carbon in the phenyl group. When a carbon atom on the alkyl side chain not only is attached to two other carbons on the alkyl side chain and to a carbon atom of an alkyl group branch but also is attached to a carbon atom of the phenyl group, the resulting alkyl-phenyl-alkane is referred to as a "quaternary alkyl-phenyl-alkane" or simply a "quat." Thus, quats comprise alkyl-phenyl-alkanes having the general formula m-alkyl-m-phenyl-alkane. If the quaternary carbon is the second carbon atom numbered from an end of the alkyl side chain, the resulting 2-alkyl-2-phenyl-alkane is referred to as an "end quat." If the quaternary carbon is any other carbon atom of the alkyl side chain, as in the second BAB example, then the resulting alkyl-phenyl-alkane is referred to as an "internal quat." In known processes for producing BAB, a relatively high proportion, typically greater than 10 mol-%, of the BAB is internal quats.

About thirty years ago it became apparent that household laundry detergents made of BABS were gradually polluting rivers and lakes. Investigation into the problem led to the recognition that BABS were slow to biodegrade. Solution of the problem led to the manufacture of detergents made of linear alkylbenzene sulfonates (LABS), which were found to biodegrade more rapidly than BABS. Today, detergents made of LABS are manufactured worldwide. LABS are manufactured from another type of alkylbenzenes called linear alkylbenzenes (LAB). The standard process used by the petrochemical industry for producing LAB consists of dehydrogenating linear paraffins to linear olefins and then alkylating benzene with the linear olefins in the presence of a catalyst such as HF or a solid catalyst. LAB are phenylalkanes comprising a linear aliphatic alkyl group and a phenyl group and have the general formula n-phenyl-alkane. LAB has no alkyl group branches, and consequently the linear aliphatic alkyl group normally has two primary carbon atoms (i.e., n≧2). Another characteristic of LAB that is produced by the standard LAB process is that the phenyl group in LAB is usually attached to any secondary carbon atom of the linear aliphatic alkyl group. In LAB produced using HF catalyst the phenyl group is slightly more likely to attach to a secondary carbon near the center as opposed to near the end of the linear aliphatic alkyl group, while in LAB produced by the Detal™ process approximately 25-35 mol-% of n-phenyl-alkanes are 2-phenyl-alkanes. U.S. Pat. Nos. 4,301,316 and 4,301,317 teach the preparation of LAB comprising 2-phenyl-alkanes using aluminum chloride, sulfuric acid, HF, and solid catalysts.

Over the last few years, other research has identified certain modified alkylbenzene sulfonates, which are referred to herein as MABS, which are different in composition from all alkylbenzene sulfonates used currently in commerce, including BABS and LABS, and from all alkylbenzene sulfonates produced by prior alkylbenzene processes, including those which alkylate aromatics using catalysts such as HF, aluminum chloride, silica-alumina, fluorided silica-alumina, zeolites, and fluorided zeolites. MABS also differ from these other alkylbenzene sulfonates by having improved laundry cleaning performance, hard surface cleaning performance, and excellent efficiency in hard and/or cold water, while also having biodegradability comparable to that of LABS.

MABS can be produced by sulfonating a third type of alkylbenzenes called modified alkylbenzenes (MAB), and the desired characteristics of MAB are determined by the desired solubility, surfactancy, and biodegradability properties of MABS. MAB comprises a large number of phenyl-alkanes, some of which may be phenyl-alkanes that are found in LAB and some of which may be phenyl-alkanes that are found in BAB, but the phenyl-alkanes that are found in BAB are not desirable phenyl-alkanes for MAB. The phenyl-alkanes in MAB are phenyl-alkanes comprising a lightly branched aliphatic alkyl group and a phenyl group and has the general formula $(m_i\text{-alkyl}_l)_i$-n-phenyl-alkane. Phenyl-alkanes in MAB usually have only one alkyl group branch, and the alkyl group branch is a methyl group, which is preferred, an ethyl group, or an n-propyl group, so that, where there is only one alkyl group branch and n≠1, the aliphatic alkyl group in MAB has three primary carbons. A preferred MAB phenyl-alkane is a monomethyl-phenyl-alkane. However, the aliphatic alkyl group in a MAB phenyl-alkane may have two primary carbon atoms if there is only one alkyl group branch and n=1, or, if there are two alkyl group branches and n≠1, four primary carbons. Thus, the first characteristic of MAB is that the average number of primary carbons in the aliphatic alkyl groups of the phenyl-alkanes in MAB is intermediate between that in BAB and that in LAB. Another characteristic of MAB is that it contains a high proportion of 2-phenyl-alkanes, namely that from about 40 to about 100% of phenyl groups are attached selectively to the second carbon atom as numbered from an end of the alkyl side chain.

A final characteristic of the MAB alkylate is that the MAB has a relatively low proportion of internal quats. Some internal quats such as 5-methyl-5-phenyl-undecane produce MABS that has shown slower biodegradation, but end quats such as 2-methyl-2-phenyl-undecane produce MABS that show biodegradation similar to that of LABS. For example, biodegradation experiments show that in a porous pot activated sludge treatment, the ultimate biodegradation was greater for sodium 2-methyl-2-undecyl [$C^{14}$] benzenesulfonate than for sodium 5-methyl-5-undecyl [$C^{14}$] benzenesulfonate. See the article entitled "Biodegradation of Coproducts of Commercial Linear Alkylbenzene Sulfonate," by A. M. Nielsen et al., in Environmental Science and Technology, Vol. 31, No. 12, 3397-3404 (1997). A relatively low proportion, typically less than 10 mol-%, of MAB is internal quats.

Because of the advantages of MABS over other alkylbenzene sulfonates, catalysts and processes are sought that produce MAB with a selectivity to 2-phenyl-alkanes and selectivity away from internal quaternary phenyl-alkanes.

SUMMARY OF THE INVENTION

In one aspect, this invention is a process for the production of phenyl-alkanes, in particular modified alkylbenzenes (MAB), by adsorptive separation, dehydrogenation, and alkylation. The process is characterized by the composition of the adsorbent and desorbent pair used in the process. The adsorbent used is silicalite and the preferred desorbent comprises a $C_5$-$C_8$ linear paraffin, a $C_5$-$C_8$ cycloparaffin, and/or a branched paraffin such as isooctane.

A broad embodiment of this invention may be characterized as a process for producing phenyl-alkanes. A paraffinic feed stream comprising a $C_8$-$C_{28}$ acyclic paraffin having 2 or 3 primary carbon atoms and at least one other acyclic paraffin pass to an adsorption zone. The feed stream has a first concentration of the acyclic paraffin having 2 or 3 primary carbon atoms. The adsorption zone comprises a bed of an adsorbent comprising silicalite at adsorption promoting conditions to selectively adsorb the acyclic paraffin having 2 or 3 primary carbon atoms. A desorbent stream comprising at least one component selected from the group consisting of a $C_5$-$C_8$ cycloparaffin, a $C_5$-$C_8$ normal paraffin, and a $C_5$-$C_8$ branched paraffin contacts the bed of adsorbent. An adsorption extract having a second concentration of the acyclic hydrocarbon having 2 or 3 primary carbon atoms is recovered from the adsorption zone. The second concentration is greater than the first concentration. At least a portion of the adsorption extract passes to a dehydrogenation zone, which is operated at dehydrogenation conditions sufficient to dehydrogenate the acyclic paraffin having 2 or 3 primary carbon atoms. A dehydrogenated product stream comprising a $C_8$-$C_{28}$ acyclic monoolefin having 2 or 3 primary carbon atoms is recovered from the dehydrogenation zone. An aromatic feedstock comprising a phenyl compound and at least a portion of the dehydrogenated product stream comprising the acyclic monoolefin pass to an alkylation zone. The alkylation zone operates at alkylation conditions sufficient to alkylate the phenyl compound with the acyclic monoolefin in the presence of an alkylation catalyst to form a phenyl-alkane comprising a molecule having one phenyl portion and one $C_8$-$C_{28}$ aliphatic alkyl portion. The aliphatic alkyl portion has 2 or 3 primary carbon atoms and no quaternary carbon atoms except for any quaternary carbon atom bonded by a carbon-carbon bond with a carbon atom of the phenyl portion. The alkylation has a selectivity to 2-phenyl-alkanes of from 40 to 100 and a selectivity to internal quaternary phenyl-alkanes of less than 10. The phenyl-alkane is recovered from the alkylation zone. In a preferred embodiment, the alkylation has a selectivity to phenyl-alkanes having an aliphatic alkyl portion containing a quaternary carbon atom not bonded by a carbon-carbon bond with a carbon atom of the phenyl portion of less than 10, and more preferably less than 1.

This invention, when used for detergent alkylation, produces detergents that meet the increasingly stringent requirements of 2-phenyl-alkane selectivity and internal quaternary phenyl-alkane selectivity for the production of modified alkylbenzenes (MAB). Thus, in another process aspect of this invention, the MAB, in turn, can be sulfonated to produce modified linear alkylbenzene sulfonates (MABS), which have improved cleaning effectiveness in hard and/or cold water while also having biodegradability comparable to that of linear alkylbenzene sulfonates.

In yet other aspect, this invention is the MAB and MABS compositions produced by the processes of this invention. The processes of this invention produce particular MAB and MABS products having aliphatic alkyl chains with specially tailored extents of branching that are not necessarily the same as those of the prior art processes.

This invention is, in another of its aspects, the use of MAB and MABS produced by the process of this invention as a lubricant and as a lubricant additive, respectively.

Additional aspects and embodiments are described in the following description of this invention.

Information Disclosure

LAB processes are described in the book edited by Robert A. Meyers entitled *Handbook of Petroleum Refining Processes*, (McGraw-Hill, N.Y., Second Edition, 1997) at pages 1.53 to 1.66, the teachings of which are incorporated herein by reference. Paraffin dehydrogenation processes are described in the Meyers book at pages 5.11 to 5.19, the teachings of which are incorporated herein by reference.

PCT International Publication Nos. WO 99/05082, WO 99/05084, 99/05241, and WO 99/05243, all four of which were published on Feb. 4, 1999, and which are incorporated herein by reference, disclose alkylation processes for uniquely lightly branched or delinearized alkylbenzenes. PCT International Publication No. WO99/07656, published on Feb. 18, 1999, which is incorporated herein by reference, discloses processes for such alkylbenzenes using adsorptive separation.

U.S. Pat. No. 5,276,231 (Kocal et al.) describes a process for the production of linear alkylaromatics with selective removal of aromatic by-products of the paraffin dehydrogenation zone of the process. In U.S. Pat. No. 5,276,231, paraffins from the paraffin column of the alkylation zone are recycled to the reactor of the dehydrogenation zone, with or without selective hydrogenation of any monoolefins in the paraffin recycle stream. U.S. Pat. No. 5,276,231 also teaches the selective hydrogenation of diolefinic by-products from the dehydrogenation zone. The teachings of U.S. Pat. No. 5,276,231 are incorporated herein by reference.

U.S. Pat. Nos. 5,196,574 (Kocal) and 5,344,997 (Kocal) describe alkylation of aromatics using a fluorided silica-alumina catalyst. U.S. Pat. No. 5,302,732 (Steigleder et al.) describes alkylation of aromatics using an ultra-low sodium silica-alumina catalyst. The teachings of U.S. Pat. Nos. 5,196,574, 5,302,732, and 5,344,997 are incorporated herein by reference.

U.S. Pat. No. 5,196,625 discloses a dimerization step which produces olefins having a carbon-carbon double bond between the third and fourth, between the fourth and fifth, and between the sixth and seventh carbon atoms of the aliphatic alkenyl chain.

U.S. Pat. Nos. 4,301,316 and 4,301,317 teach the preparation of LAB comprising 2-phenyl-alkanes using aluminum chloride, sulfuric acid, HF, and solid catalysts.

DETAILED DESCRIPTION OF THE INVENTION

Figure 1:
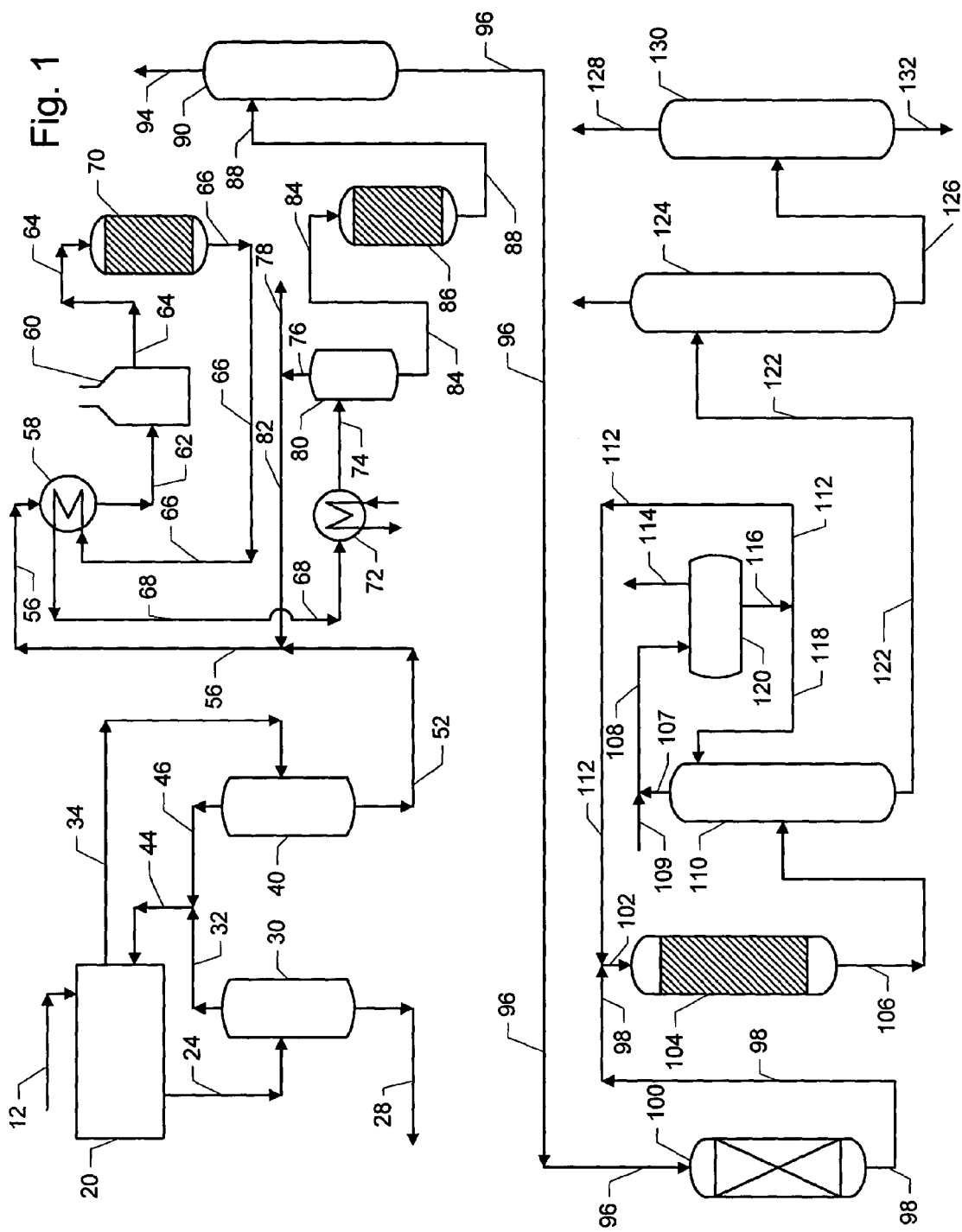
FIG. 1 shows an embodiment of the invention.

A feed mixture comprising a paraffin and a feedstock comprising a phenyl compound are consumed in the subject process. The feed mixture preferably comprises one or more acyclic paraffins having a total number of carbon atoms of from about 8 to about 28. The acyclic paraffin is preferably a "lightly branched paraffin," which as used herein, refers to a paraffin having three or four primary carbon atoms and for which none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. Normally, the lightly branched paraffin has a total number of from 9 to 16 carbon atoms, preferably from 10 to 14 carbon atoms, and highly preferably from 10 to 13 carbon atoms. The lightly branched paraffin generally comprises an aliphatic alkane having the general formula of $(p_i\text{-alkyl}_i)_i$-alkane. The lightly branched paraffin consists of an aliphatic alkyl chain, which is referred to by "alkane" in the $(p_i\text{-alkyl}_i)_i$-alkane formula, and is the longest straight chain of the lightly branched paraffin. The lightly branched paraffin also consists of one or more alkyl group branches, each of which is attached to the aliphatic alkyl chain and is designated by a corresponding "$(p_i\text{-alkyl}_i)$," in the $(p_i\text{-alkyl}_i)_i$-alkane formula. If it is possible to select two or more chains of equal lengths as the aliphatic alkyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $p_i$ of the aliphatic alkyl chain. The aliphatic alkyl chain is numbered from one end to the other, the direction being chosen so as to give the lowest numbers possible to the carbon atoms having alkyl group branches.

The lightly branched paraffins comprise generally more than 30 mol-% and preferably more than 70 mol-%, of the feed mixture to the subject process. The alkyl group branch or branches of the lightly branched paraffin are generally selected from methyl, ethyl, and propyl groups, with shorter and normal branches being preferred. Preferably, the lightly branched paraffin has only one alkyl group branch. Lightly branched paraffins having either two alkyl group branches or four primary carbon atoms comprise generally less than 30 mol-%, and preferably less than about 15 mol-%, of the total lightly branched paraffins. Lightly branched paraffins having either one alkyl group branch or three primary carbon atoms comprise preferably more than 85 mol-% of the total lightly branched paraffins. Any alkyl group branch can be bonded to any carbon on the aliphatic alkyl chain.

The feed mixture may also contain one or more nonbranched (linear) or normal paraffin molecules having a total number of carbon atoms per paraffin molecule of generally from about 8 to about 28, normally from 9 to 16, more preferably from 10 to 14 carbon atoms, and highly preferably from 10 to 13 carbon atoms. Two carbon atoms per nonbranched paraffin molecule are primary carbon atoms and the remaining carbon atoms are secondary carbon atoms. A secondary carbon atom is a carbon atom which, although possibly bonded also to other atoms besides carbon, is bonded to only two carbon atoms. The concentration of nonbranched paraffins in the feed mixture is often above 0.3 mol-%.

In addition to lightly branched and nonbranched paraffins, other acyclic compounds may also be in the feed mixture. Other such acyclic compounds are more highly branched than the lightly branched paraffins. However, on dehydrogenation such highly branched paraffins tend to form highly branched monoolefins which on alkylation tend to form BAB. For example, paraffin molecules consisting of at least one quaternary carbon atom tend on dehydrogenation followed by alkylation to form phenyl-alkanes that have in the aliphatic alkyl portion a quaternary carbon atom that is not bonded by a carbon-carbon bond with a carbon atom of the phenyl portion. Therefore, the quantity of these highly branched paraffins charged to the process is preferably minimized. Paraffin molecules consisting of at least one quaternary carbon atom generally comprise less than 10 mol-%, preferably less than 5 mol-%, more preferably less than 2 mol-%, and most preferably less than 1 mol-% of the feed mixture.

The production of the feed mixture is not an essential element of this invention, and any suitable method for producing the feed mixture may be used. But, since the carbon number range of the feed mixture desired for the production of MAB is normally between 9 and 16, with 10 to 14 often being preferred and a range of 10-13 being highly preferred for the subject process due to improved detergent properties, and since this range corresponds to paraffins boiling in the kerosene boiling point range, kerosene fractions produced in petroleum refineries either by crude oil fractionation or by conversion processes therefore form suitable feed mixture precursors. Thus, feed mixtures which can be utilized in the process of this invention will typically be derived from kerosene and prepared either by prior separation step(s) or by relatively specific oligomerization or alkylation reactions. Such feed mixture preparation methods are inherently imprecise and produce a mixture of compounds. The feed mixtures to the process may contain quantities of paraffins having multiple branches and paraffins having multiple carbon atoms in the branches, cycloparaffins, branched cycloparaffins, or other compounds having boiling points relatively close to the desired compound isomer. Thus, the feed mixtures to the process of this invention can also contain sizable quantities of aromatic hydrocarbons.

Fractions recovered from crude oil by fractionation will typically require hydrotreating for removal of sulfur and/or nitrogen prior to being fed to the subject process. The boiling point range of the kerosene fraction can be adjusted by prefractionation to adjust the carbon number range of the paraffins. In an extreme case the boiling point range can be limited such that only paraffins of a single carbon number predominate. Kerosene fractions contain a very large number of different hydrocarbons and the feed mixture to the subject process can therefore contain 200 or more different compounds.

It is expected, however, that separation rather than oligomerization or other forms of synthesis will provide a lower cost adequate feed mixture and will therefore be the predominate source of the feed mixture. A preferred method for the production of the feed mixture is the separation of nonbranched (linear) hydrocarbons or lightly branched hydrocarbons from a kerosene boiling range petroleum fraction. Several known processes that accomplish such a separation are known. One process, the UOP Molex™ process, is an established, commercially proven method for the liquid-phase adsorption separation of normal paraffins from isoparaffins, cycloparaffins, and aromatics using the UOP Sorbex separation technology. See Chapters 10.3 and 10.7 in the book entitled *Handbook of Petroleum Refining Process*, Second Edition, edited by Robert A. Meyers, published by McGraw-Hill, N.Y., 1997. Another suitable, established, and proven process is the UOP Kerosene Isosiv™ Process, which employs vapor-phase adsorption for separating normal paraffins from nonnormal paraffins using molecular sieves in an adsorber vessel. See Chapter 10.6 in the above-mentioned Meyers book. Another vapor-phase adsorption process, which uses ammonia as the desorbent, is described in the paper entitled "Exxon Chemical's Normal Paraffins Technologies," written by R. A. Britton, which was prepared for presentation at the AIChE Annual 1991 National Meeting, Design of Adsorption Systems Session, Los Angeles, Calif., Nov. 21, 1991, and in the article written by W. J. Asher et al. and starting at page 134 of Hydrocarbon Processing, Vol. 48, No. 1 (January 1969). Chapter 11 of the book entitled *Principles of Adsorption and Adsorption Processes*, by Douglas M. Ruthven, published by John Wiley and Sons, New York, 1984, describes other adsorption separation processes. The streams charged to these above-mentioned separation processes, which comprise branched paraffins that are more highly branched than the lightly branched paraffins, can be obtained by extraction or by suitable oligomerization processes. However, the above-mentioned adsorption separation processes are not necessarily equivalent in terms of acceptable concentrations of impurities such as sulfur in their respective streams charged to their respective processes.

The raffinate stream of an adsorptive separation process, such as the UOP Molex™ process which selectively recovers the nonbranched (linear) paraffins in an extract stream, is an especially preferred feed mixture for the subject process. The raffinate stream from such a process will be free of contaminants such as sulfur or nitrogen containing compounds, and will also have a suitably low concentration of nonbranched paraffins and olefins. The use of such a raffinate stream as the feed mixture allows integration of the subject process into an existing LAB facility, with the two adsorptive separation steps being performed in series. The separately recovered normal paraffin stream and feed mixture can then be processed in a variety of ways. For instance, each of the nonbranched paraffin stream and the feed mixture could be processed independently via dehydrogenation and aromatic alkylation to produce two separate products. Alternatively, the nonbranched paraffin stream and the feed mixture could be used to form a desired paraffin blend. That is, the stream charged to the dehydrogenation zone of the subject process can comprise the product of the separation zone of the subject process plus from about 10 to about 50 vol-% nonbranched paraffins. In another alternative, olefins derived from the nonbranched paraffin stream and the feed mixture could be used to form a desired blend prior to alkylation, so that the stream charged to the alkylation zone of the subject process can comprise the product of the separation section of the subject process plus from about 10 to about 50 vol-% nonbranched olefins.

The composition of a mixture of linear, lightly branched, and branched paraffins, such as that of the feed mixture to the subject process or of the stream charged to the above-mentioned adsorption separation processes, can be determined by analytical methods that are well-known to a person of ordinary skill in the art of gas chromatography and need not be described here in detail. The article written by H. Schulz, et al. and published starting at page 315 of the Chromatographia 1, 1968, which is incorporated herein by reference, describes a temperature-programmed gas chromatograph apparatus and method that is suitable for identifying components in complex mixtures of paraffins. A person of ordinary skill in the art can separate and identify the components in a mixture of paraffins using essentially the apparatus and method described in the article by Schulz et al.

The aromatic-containing feedstock to the subject process comprises a phenyl compound, which is benzene when the process is detergent alkylation. In a more general case, the phenyl compound of the aromatic feedstock may be alkylated or otherwise substituted derivatives or of a higher molecular weight than benzene, including toluene, ethylbenzene, xylene, phenol, naphthalene, etc., but the product of such an alkylation may not be as suitable a detergent precursor as alkylated benzenes.

For purposes of discussion, the subject process may be divided into an adsorptive separation section, a dehydrogenation section, and an alkylation section.

The adsorptive separation section is directed to the separation and recovery of acyclic, lightly branched paraffins from the feed mixture. This separation can be performed in a batch or continuous mode including the use of two or more adsorbent beds in cyclic operation. In this mode one or more beds are used for the separation while another bed is being regenerated. Significant operational and economic advantages accrue to performing the separation on a continuous basis which produces a product of uniform composition. The preferred method of achieving continuous operation and uniform products is by the use of simulated moving bed technology. Also, the preferred paraffins separated from the feed mixture are monomethyl paraffins. Therefore, the following description of the adsorptive separation section of the subject process is basically in terms of the separation of various monomethyl paraffins from other hydrocarbons as it would be performed in large scale simulated moving bed (SMB) units. This description is, however, not intended to limit the invention as set forth in the claims.

Most SMB adsorptive separation units simulate countercurrent movement of the adsorbent and the feed stream. This simulation is performed using established commercial technology wherein the adsorbent is held fixed in place as a number of subbeds retained in one or more cylindrical adsorbent chambers. The positions at which the streams involved in the process enter and leave the chambers are slowly shifted from subbed to subbed along the length of the adsorbent chambers so that the streams enter or leave different subbeds as the operational cycle progresses. Normally there are at least four streams (feed, desorbent, extract and raffinate) employed in this procedure, and the location at which the feed and desorbent streams enter the chamber and the extract and raffinate streams leave the chamber are simultaneously shifted in the same direction at set intervals. Each periodic incremental shift in the location of these transfer points delivers or removes liquid from a different subbed of adsorbent within the chamber. This shifting could be performed using a dedicated line for each stream at the entrance to each subbed. However, this would greatly increase the cost of the process and therefore the lines are reused. Only one line is normally employed for each subbed, and each bed line carries one of the four process streams at some point in the cycle. This simulation procedure normally also includes the use of a variable flow rate pump which pushes liquid leaving one end of the adsorbent vessel(s) to the other end in a single continuous loop.

Simulated moving bed processes typically include at least three or four separate steps which are performed sequentially in separate zones within a mass of adsorbent retained in one or more vertical cylindrical adsorption chambers. Each of these zones normally is formed from a plurality of beds of adsorbent, sometimes referred to as subbeds, with the number of beds per zone ranging from 2 or 3 up to 8 to 10. The most widely practiced commercial process units typically contain about 24 beds. All of the beds are contained in one or more vertical vessels referred to herein collectively as the adsorbent chamber. The beds are structurally separated from one another by a horizontal liquid collection/distribution grid. Each grid is connected to a transfer line defining a transfer point at which process streams such as the feed, raffinate, and extract streams enter or leave the vertical adsorption chambers.

The general technique employed in the performance of a simulated moving bed adsorptive separation is well described in the open literature. For instance a general description of a process directed to the recovery of para-xylene by SMB was presented at page 70 of the September 1970 edition of *Chemical Engineering Progress* (Vol. 66, No 9). A generalized description of the process with an emphasis on mathematical modeling was given at the International Conference on "Fundamentals of Adsorption", Schloss Elmau, Upper Bavaria, Germany on May 6-11, 1983 by D. B. Broughton and S. A. Gembicki. Numerous other available references describe many of the mechanical parts of a simulated moving bed system, including rotary valves for distributing various liquid flows to the bed lines, the internals of the adsorbent chambers and control systems.

Countercurrent simulated moving bed systems are described in many available references, such as U.S. Pat. No. 2,985,589, incorporated herein by reference for its teaching of the practice of simulated moving bed adsorptive separation processes. Cyclic advancement of the input and output streams of this simulation can be accomplished by a manifolding system or by rotary disc valves as shown in U.S. Pat. Nos. 3,040,777 and 3,422,848. Equipment utilizing these principles can vary in size from the pilot plant scale shown in U.S. Pat. No. 3,706,812 to commercial petrochemical plant scale, with flow rates ranging from a few cc per hour to many thousands of gallons per hour. Large scale plants normally employ rotary valves having a port for each transfer line while small scale and high pressure units tend to use valves having only two or three ports. The invention may also be practiced in a cocurrent process, like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals.

During the adsorption step of the process a feed mixture containing a mixture of compounds is contacted with the adsorbent at adsorption conditions and one or more compound(s) or a class of compounds is selectively adsorbed and retained by the adsorbent while the other compounds of the feed mixture are relatively unabsorbed. Normally the desired compound is adsorbed. The feed mixture may contain a large variety of compounds including isomers of the desired compound. For instance, a mixed xylene feed stream may contain ethylbenzene and/or $C_9$ aromatics and can be processed to recover a specific isomer by a suitable adsorbent/desorbent pair operated at suitable conditions.

Differing sieve/desorbent combinations are used for different separations. For instance, X zeolites, specifically X zeolites exchanged with barium or barium and potassium ions at their exchangeable sites, are the preferred adsorbents for p-xylene recovery from xylene mixtures. When the adsorbent contains a near equilibrium loading of the more selectively adsorbed compound, it is referred to as a "rich" adsorbent. In the next step of the process, the unabsorbed (raffinate) components of the feed mixture are then removed from the interstitial void spaces between the particles of adsorbent and from the surface of the adsorbent. This depleted liquid and any desorbent which becomes admixed with it during passage through the adsorption zone in this step is removed from the process as part of a process stream referred to as the raffinate stream. The adsorbed compound is then recovered from the rich adsorbent by contacting the rich adsorbent with a stream comprising the desorbent material at desorption conditions in a desorption step. The desorbent displaces the desired compound to form an extract stream, which is normally transferred to a fractionation zone for recovery of the desired compound from the extract stream containing a mixture of the desired compound and desorbent. It should be noted that in some instances the desired product of the process can be in the raffinate stream rather than the extract stream and the process adsorbs undesired compounds.

For purposes of this description, various terms used herein are defined as follows. A "feed mixture" is a mixture containing one or more extract components and one or more raffinate components to be separated by the adsorption section of the subject process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or class of compound that is less selectively adsorbed. The term "desorbent material" means generally a material capable of and used for desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

At least portions of the extract stream and the raffinate stream are passed to separation means, typically fractional distillation columns, where at least a portion of desorbent material is recovered and an extract product and a raffinate product are produced. The stream containing the undesired compound may be recycled to isomerization. The extract stream may be rich in the desired compound or may only contain an increased concentration. When used relative to a process stream the term "rich" is intended to indicate a concentration of the indicated compound or class of compounds greater than 50 mole percent.

It has become customary in the art to group the numerous beds in the adsorption chambers into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In the desorption zone or Zone III of the adsorbent chamber(s) the desired isomer is released from the adsorbent by exposing and flushing the adsorbent with the desorbent (mobile phase). The released desired isomer and accompanying desorbent are removed from the adsorbent in the extract stream. Zone IV is a quantity of adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorption, Liquid Separation section of the *Kirk-Othmer Encyclopedia of Chemical Technology*. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

It has been found that the objectives of this invention can be achieved by employing a novel adsorbent-desorbent pair comprising, on the one hand, an adsorbent comprising silicalite and, on the other hand, a desorbent containing a linear paraffin and/or cycloparaffin; a desorbent containing a linear paraffin and a branched paraffin; or a desorbent containing a linear paraffin, a cycloparaffin, and a branched paraffin. The preferred desorbent is a mixture of a $C_5$ to $C_8$ normal paraffin and a cycloparaffin, with or without a $C_5$ to $C_8$ branched paraffin. The preferred branched paraffin for the desorbent is isooctane. An adsorbent-desorbent pair comprising an adsorbent comprising silicalite and a desorbent containing a branched paraffin or containing a cycloparaffin and a branched paraffin may be used in practicing this invention but is not preferred.

The preferred adsorbent comprises silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," *Nature*, Vol. 271, Feb. 9, 1978 which is incorporated herein by reference for its description and characterization of silicalite. Silicalite is a hydrophobic crystalline silica molecular sieve having an MFI type structure of intersecting bent-orthogonal channels formed with two cross-sectional geometries, 6 Å circular and 5.1-5.7 Å elliptical on the major axis. This gives silicalite great selectivity as a size selective molecular sieve. Due to its aluminum free structure composed of silicon dioxide silicalite does not show ion-exchange behavior. Thus silicalite is not a zeolite.

The practice of the subject invention requires no significant variation in operating conditions, adsorbent or desorbent composition within the adsorbent chambers or during different process steps. That is, the adsorbent preferably remains at the same temperature and pressure throughout the process.

The active component of the adsorbent is normally used in the form of small agglomerates having high physical strength and attrition resistance. The agglomerates contain the active adsorptive material dispersed in an amorphous, inorganic matrix referred to as the binder and having channels and cavities therein which enable fluid access to the adsorptive material. Methods for forming the crystalline powders into such agglomerates include the addition of an inorganic binder, generally a clay comprising a silicon dioxide and aluminum oxide, to a high purity adsorbent powder in a wet mixture. Silica is a suitable binder. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, macrospheres or granules having a desired particle range, preferably from about 16 to about 60 mesh (Standard U.S. Mesh)

(1.9 mm to 250 microns). Clays of the kaolin type, water permeable organic polymers or silica are generally used as binders.

Those skilled in the art will appreciate that the performance of a particular adsorbent is often greatly influenced by a number of factors not related to its composition such as operating conditions, feed stream composition, and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the water content of the adsorbent results in an LOI at 900° C. of less than 7.0 wt-% and preferably within the range of from 0 to 4.0 wt-%.

A silicalite or other microporous active component of the adsorbent will ordinarily be in the form of small crystals present in the adsorbent particles in amounts ranging from about 75 to about 98 wt-% of the particle based on volatile-free composition. Volatile-free compositions are generally determined after the adsorbent has been calcined at 900° C. in order to drive off all volatile matter. The remainder of the adsorbent will generally be the inorganic matrix of the binder present in intimate mixture with the small particles of the active adsorbent material. This matrix material may be an adjunct of the manufacturing process for the active adsorbent material, for example, from the intentionally incomplete purification of the silicalite during its manufacture.

In the practice of the present invention, a feed mixture comprising one or more monomethyl branched hydrocarbons and at least one nonnormal hydrocarbon of like carbon number but different structure is passed through one or more beds of an adsorbent which selectively adsorbs the monomethyl branched hydrocarbon while permitting other components of the feed stream to pass through the adsorption zone in an unchanged condition. At some point in time based upon the remaining capacity of the adsorbent, the flow of the feed stream through the adsorbent bed is stopped and the adsorption zone is then flushed to remove nonadsorbed materials surrounding the adsorbent. Thereafter the desired isomer is desorbed from the adsorbent by passing a desorbent stream through the adsorbent bed. The desorbent material is commonly also used to flush nonadsorbed materials from the void spaces around and within the adsorbent.

The selectivity, ($\beta$), of an adsorbent/desorbent pair is defined as the ratio of the two components in the adsorbed phase divided by the ratio of the same two components in the unabsorbed phase at equilibrium conditions. Relative selectivity is given by the equation:

$$\text{Selectivity} = \frac{\text{wt. percent } C/\text{wt. percent } D_A}{\text{wt. percent } C/\text{wt. percent } D_U}$$

where C and D are two components of the feed stream represented in weight percent and the subscripts A and U represent the adsorbed and unabsorbed phases, respectively. The equilibrium conditions are determined when the feed stream passing over a bed of adsorbent does not change composition, in other words, when there is no net transfer of material occurring between the unabsorbed and adsorbed phases.

Relative selectivity can be expressed not only for one feed stream compound as compared to another but can also be expressed between any feed mixture component and the desorbent material.

Where selectivity of two components approaches 1.0, there is no preferential adsorption of one component by the adsorbent with respect to the other; they are both adsorbed to about the same degree with respect to each other. As $\beta$ becomes less than or greater than 1.0, there is a preferential adsorption by the adsorbent for one component with respect to the other. When comparing the selectivity of the adsorbent for component C over component D, a $\beta$ larger than 1.0 indicates preferential adsorption of component C within the adsorbent. A $\beta$ less than 1.0 would indicate that component D is preferentially adsorbed leaving an unabsorbed phase richer in component C and an adsorbed phase richer in component D.

An important characteristic of an adsorbent is the rate of exchange of the desorbent for the extract component of the feed mixture or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which insures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

Adsorption conditions in general include a temperature range of from about 20 to about 250° C., with from about 40 to about 150° C. being more preferred. Temperatures from 80° C. to 140° C. are highly preferred. Adsorption conditions also preferably include a pressure sufficient to maintain the process fluids in liquid phase; which may be from about atmospheric to 600 psi(g). Desorption conditions generally include the same temperatures and pressure as used for adsorption conditions. Slightly different conditions may be preferred depending on the composition of the adsorbent and the feed stream.

The preferred desorbent comprises a mixture of a normal paraffin on the one hand and a cycloparaffin (naphthene) or branched paraffin such as isooctane on the other hand, but the desorbent stream may comprise a single component. In the mixture, the normal paraffin and cycloparaffin, or the normal paraffin and isooctane, may have the same carbon number, such as in the range of 5 to 8. Preferred cycloparaffins are cyclopentane, cyclohexane and methyl cyclohexane. The preferred normal paraffins are n-pentane and n-hexane, and the desorbent may range from 0 to 100% normal paraffin. Normal paraffins are strong desorbents and n-hexane is actually the strongest desorbent of these compounds. A blend of normal paraffins and cycloparaffins, or of normal paraffins and isooctane, is often desirable to adjust the strength of the desorbent stream. These blends may contain from about 10 to 90 vol-% cycloparaffin or isooctane, with the remainder being the normal paraffin. The desorbent may also be 100% cycloparaffin. The preferred branched paraffin is isooctane.

The extract stream comprises paraffins having a total number of carbon atoms per paraffin molecule of generally from about 8 to about 28, preferably from 8 to 15, and more preferably from 10 to 15 carbon atoms. The extract stream generally contains a higher concentration of lightly branched paraffins, based on the total paraffins in the extract stream, than the concentration of lightly branched paraffins in the feed mixture, based on the total paraffins in the feed mixture. The lightly branched paraffins having either two alkyl group branches or four primary carbon atoms comprise generally less than 60 mol-%, preferably less than 30 mol-%, and more preferably less than about 15 mol-%, of the total lightly branched paraffins in the extract stream or in that portion of the extract stream that passes to the dehydrogenation zone of the process. The lightly branched paraffins having either one alkyl group branch or three primary carbon atoms comprise preferably more than 85 mol-% of the total lightly branched paraffins in the extract stream or in the portion of the extract stream charged to the dehydrogenation zone. Lightly branched paraffins having only one alkyl group branch and where the sole alkyl group branch is a methyl group are referred to herein as monomethyl-alkanes and are a preferred component of the extract stream. Any alkyl group branch can be bonded to any carbon on the aliphatic alkyl chain. When present in the extract stream with the lightly branched paraffins, the linear paraffin content may be as high as, or no more than, about 75 mol-% of the total paraffins in the extract stream or in that portion of the extract stream that is charged to the dehydrogenation zone. Paraffin molecules consisting of at least one quaternary carbon atom generally comprise less than 10 mol-%, preferably less than 5 mol-%, more preferably less than 2 mol-%, and most preferably less than 1 mol-%, of the extract stream or of that portion of the extract stream that passes to the dehydrogenation zone.

The dehydrogenation section may be configured substantially in the manner shown in the drawing. Briefly, a stream containing paraffins combines with recycled hydrogen to form a dehydrogenation reactant stream that is heated and contacted with a dehydrogenation catalyst in a fixed bed maintained at dehydrogenation conditions. The effluent of the fixed catalyst bed, which is referred to herein as the dehydrogenation reactor effluent stream, is cooled, partially condensed, and passed to a vapor-liquid separator. The vapor-liquid separator produces a hydrogen-rich vapor phase and a hydrocarbon-rich liquid phase. The condensed liquid phase recovered from the separator passes to a stripping column, which removes all compounds which are more volatile than the lightest hydrocarbon which is desired to be passed to the alkylation section. The olefin-containing net stream that passes from the dehydrogenation section to the alkylation section of the process is referred to herein as the dehydrogenated product stream.

This invention is not limited to any one particular flow scheme for the dehydrogenation section, since dehydrogenation flow schemes other than that shown in the drawing are also within the scope of this invention as set forth in the claims. For example, the dehydrogenation catalyst may be in a moving catalyst bed or a fluidized bed. The dehydrogenation zone may comprise one or more catalyst-containing reaction zones with heat exchangers there between to ensure that the desired reaction temperature is maintained at the entrance to each reaction zone. One or more hot hydrogen-rich gas streams may be introduced between a first and a second reaction zone to increase the temperature of a stream passing from the first to the second reaction zone, as disclosed in U.S. Pat. No. 5,491,275 (Vora et al.) and U.S. Pat. No.5,689,029 (Vora et al.), both of whose teachings are incorporated herein by reference thereto. Each reaction zone may be operated in a continuous-type or batch-type manner for continuous or batch system. Each reaction zone may contain one or more catalyst beds. Hydrocarbons may contact any catalyst bed in an upward-, downward-, or radial-flow fashion. In a particularly compact and efficient arrangement, the contacting of the catalyst with hydrocarbons and heat exchanging may be accomplished in a heat exchanging reactor. One example of such a reactor is an isothermal reactor design using interleaved layers of plate heat exchange elements, which is described in U.S. Pat. No. 5,405,586 (Koves) which is incorporated herein by reference thereto. Another example of a reactor arrangement is disclosed in U.S. Pat. No. 5,525,311 (Girod et al.), where a reactant stream indirectly contacts a heat exchange stream and where an arrangement of corrugated heat exchange plates is used to control temperature conditions by varying the number and/or the arrangement of the corrugations along the plates. The teachings of U.S. Pat. No. 5,525,311 are incorporated herein by reference thereto.

Dehydrogenation catalysts are well known in the prior art as exemplified by U.S. Pat. Nos. 3,274,287; 3,315,007; 3,315,008; 3,745,112; 4,430,517; 4,716,143; 4,762,960; 4,786,625; and 4,827,072. It is believed that the choice of a particular dehydrogenation catalyst is not critical to the success of this invention. However, a preferred catalyst is a layered composition comprising an inner core and an outer layer bonded to the inner core, where the outer layer comprises a refractory inorganic oxide having uniformly dispersed thereon at least one platinum group (Group VIII (IUPAC 8-10)) metal and at least one promoter metal, and where at least one modifier metal is dispersed on the catalyst composition. Preferably, the outer layer is bonded to the inner core to the extent that the attrition loss is less than 10 wt-% based on the weight of the outer layer. The preferred catalyst composition is described in pending U.S. patent application Ser. No. 09/185,189, filed Nov. 3, 1998, the teachings of which are incorporated herein by reference.

The dehydrogenation conditions are selected to minimize cracking and polyolefin by-products. It is expected that typical dehydrogenation conditions will not result in any appreciable isomerization of the hydrocarbons in the dehydrogenation reactor. When contacting the catalyst, the hydrocarbon may be in the liquid phase or in a mixed vapor-liquid phase, but preferably it is in the vapor phase. Dehydrogenation conditions include a temperature of generally from about 400° C. (752° F.) to about 900° C. (1652° F.) and preferably from about 400° C. (752° F.) to about 525° C. (977° F.), a pressure of generally from about 1 kpa(g) (0.15 psi(g)) to about 1013 kpa(g) (147 psi(g)), and a LHSV of from about 0.1 to about 100 $hr^{-1}$. As used herein, the abbreviation "LHSV" means liquid hourly space velocity, which is defined as the volumetric flow rate of liquid per hour divided by the catalyst volume, where the liquid volume and the catalyst volume are in the same volumetric units. Generally for normal paraffins, the lower the molecular weight the higher the temperature required for comparable conversion. The pressure in the dehydrogenation zone is maintained as low as practicable, usually less than 345 kPa(g) (50 psi(g)), consistent with equipment limitations, to maximize chemical equilibrium advantages.

The extract stream may be admixed with a diluent material before, while, or after being flowed to the dehydrogenation zone. The diluent material may be hydrogen, steam, methane, ethane, carbon dioxide, nitrogen, argon, and the like, or a mixture thereof. Hydrogen is the preferred diluent. Ordinarily, when hydrogen is utilized as the diluent it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether, or ketone, for example, may be added to the dehydrogenation zone, either continuously or intermittently, in an amount to provide, calculated on the basis of equivalent water, about 1 to about 20,000 weight ppm of the extract stream. About 1 to about 10,000 weight ppm of water addition gives best results when dehydrogenating paraffins having from 2 to 30 or more carbon atoms.

The dehydrogenated product stream is typically a mixture of unreacted paraffins, linear (unbranched) olefins, and branched monoolefins including lightly branched monoolefins. Typically from about 0 to about 75 mol-%, and preferably from about 0 to about 50 mol-%, of the olefins in the monoolefin-containing stream from the paraffin dehydrogenation process are linear (unbranched) olefins. The dehydrogenated product may also contain monoolefins having a total number of carbon atoms of from about 8 to about 28, of which four of the carbon atoms are primary carbon atoms and one of the remaining carbon atoms is a quaternary carbon atom. Preferably, however, these monoolefins comprise less than 10 mol-%, and preferably less than 1 mol-%, of the olefins in the dehydrogenated product stream.

The dehydrogenated product stream may comprise a highly branched monoolefin or a linear (unbranched) olefin, but is preferably a lightly branched monoolefin. A "lightly branched monoolefin," as used herein, refers to a monoolefin having a total number of carbon atoms of from about 8 to about 28, of which three or four of the carbon atoms are primary carbon atoms and none of the remaining carbon atoms are quaternary carbon atoms. Preferably, the lightly branched monoolefin has a total number of from 8 to 15 carbon atoms, and more preferably from 10 to 15 carbon atoms.

The lightly branched monoolefin generally comprises an aliphatic alkene having the general formula of $(p_i\text{-alkyl}_i)_i$-q-alkene. The lightly branched monoolefin consists of an aliphatic alkenyl chain, which is referred to by "alkene" in the $(p_i\text{-alkyl}_i)_i$-q-alkene formula, and is the longest straight chain containing the carbon-carbon double bond of the lightly branched monoolefin. The lightly branched monoolefin also consists of one or more alkyl group branches, each of which is attached to the aliphatic alkenyl chain and is designated by a corresponding "$(p_i\text{-alkyl}_i)_i$" in the $(p_i\text{-alkyl}_i)_i$-q-alkene formula. If it is possible to select two or more chains of equal lengths as the aliphatic alkenyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $p_i$ of the aliphatic alkenyl chain. The double bond is between carbon number q and carbon number (q+1) of the aliphatic alkenyl chain. The aliphatic alkenyl chain is numbered from one end to the other, the direction being chosen so as to give the lowest number possible to the carbon atoms bearing the double bond.

The lightly branched monoolefin may be an alpha monoolefin or a vinylidene monoolefin, but is normally an internal monoolefin. As used herein, the term "alpha olefins" refers to olefins having the chemical formula, R—CH=$CH_2$. The term "internal olefins," as used herein, includes di-substituted internal olefins having the chemical formula R-CH=CH—R; tri-substituted internal olefins having the chemical formula R—C(R)=CH—R; and tetra-substituted olefins having the chemical formula R—C(R)=C(R)—R. The di-substituted internal olefins include beta internal olefins having the chemical formula R—CH=CH—$CH_3$. As used herein, the term "vinylidene olefins" refers to olefins having the chemical formula R—C(R)=$CH_2$. In each of the preceding chemical formulas in this paragraph, R is an alkyl group that may be identical to or different from other alkyl group(s), if any, in each formula. Insofar as permitted by the definition of the term "internal olefin", when the lightly branched monoolefin is an internal monoolefin, any two carbon atoms of the aliphatic alkenyl chain may bear the double bond. Suitable lightly branched monoolefins include octenes, nonenes, decenes, undecenes, dodecenes, tridecenes, tetradecenes, pentadecenes, hexadecenes, heptadecenes, octadecenes, nonadecenes, eicosenes, heneicosenes, docosenes, tricosenes, tetracosenes, pentacosenes, hexacosenes, heptacosenes, and octacosenes.

For lightly branched monoolefins other than vinylidene olefins, the alkyl group branch or branches of the lightly branched monoolefin are generally selected from methyl, ethyl, and propyl groups, with shorter and normal branches being preferred. By contrast, for lightly branched monoolefins that are vinylidene olefins, the alkyl group branch attached to carbon number 2 of the aliphatic alkenyl chain may be selected not only from methyl, ethyl, and propyl groups but also from alkyl groups up to and including tetradecyl ($C_{14}$) groups, while any other alkyl group branch(es) of the vinylidene olefin is (are) generally selected from methyl, ethyl, and propyl groups with shorter and normal branches being preferred. For all lightly branched monoolefins passed to the alkylation section, preferably the lightly branched monoolefin has only one alkyl group branch, but two alkyl group branches are also possible. Lightly branched monoolefins having either two alkyl group branches or four primary carbon atoms comprise generally less than 30 mol-%, and preferably less than about 15 mol-%, of the total lightly branched monoolefins passed to the alkylation section, with the remainder of the lightly branched monoolefins passed to the alkylation section having one alkyl group branch.

Monoolefins having either two alkyl group branches or four primary carbon atoms and a quaternary carbon atom comprise generally less than 10 mol-%, and preferably less than about 1 mol-%, of the total lightly branched monoolefins passed to the alkylation section. Lightly branched monoolefins having either one alkyl group branch or three primary carbon atoms comprise preferably more than 85 mol-% of the total lightly branched monoolefins passed to the alkylation section. Lightly branched monoolefins having only one alkyl group branch and where the sole alkyl group branch is a methyl group are referred to herein as monomethyl-alkenes and are a preferred component of the dehydrogenated product stream. Except for the alkyl group branch attached to carbon number 2 of the aliphatic alkenyl chain in a vinylidene olefin, any alkyl group branch can be bonded to any carbon on the aliphatic alkenyl chain.

Although vinylidene monoolefins may be present in the dehydrogenated product stream, they are normally a minor component and have a concentration of usually less than 0.5 mol-%, and more commonly less than 0.1 mol-%, of the olefins in the dehydrogenated product stream. Therefore, in the description that follows hereinafter, all references to the lightly branched monoolefins in general and to the dehydrogenated product stream in particular will assume that no vinylidene monoolefins are present.

The skeletal structures of the monoolefins in a mixture comprising lightly branched monoolefins can be determined by analytical methods that are well-known to a person of ordinary skill in the art of gas chromatography and need not be described here in detail. A person of ordinary skill in the art can modify the apparatus and method in the previously mentioned article by Schulz et al. to equip the injector with a hydrogenator insert tube in order to hydrogenate the lightly branched monoolefins to lightly branched paraffins in the injector. The lightly branched paraffins are then separated and identified using essentially the apparatus and method described in the article by Schulz et al. This apparatus and method, however, will not determine the location of the carbon-carbon double bond in any of the monoolefins in the mixture.

In addition to the lightly branched monoolefin, other acyclic compounds may be charged to the alkylation section via the dehydrogenated product stream. One of the advantages of this invention is that the stream containing the lightly branched monoolefins can be passed directly to the alkylation reaction section despite the fact that that stream also contains acyclic paraffins having the same number of carbon atoms as the lightly branched monoolefins. Thus, this invention avoids the need to separate the paraffins from the monoolefins prior to passing to the alkylation section. Other acyclic compounds include nonbranched (linear) olefins and monoolefins. Nonbranched (linear) olefins which may be charged have a total number of carbon atoms per paraffin molecule of generally from about 8 to about 28, preferably from 8 to 15, and more preferably from 10 to 13 carbon atoms. Two carbon atoms per nonbranched olefin molecule are primary carbon atoms and the remaining carbon atoms are secondary carbon atoms. The nonbranched olefin may be an alpha monoolefin but is preferably an internal monoolefin. To the extent allowed by the definition of the term "internal olefin", when the nonbranched monoolefin is an internal monoolefin, any two carbon atoms of the aliphatic alkenyl chain may bear the double bond. When present in the dehydrogenated product stream with the lightly branched monoolefins, the linear olefin content may be as high as, or no more than, about 75 mol-% of the total monoolefins in the dehydrogenated product stream, but is generally less than about 60 mol-% of the total monoolefins in the dehydrogenated product stream.

Because of the possible presence in the dehydrogenated product stream of linear monoolefins, in addition to the lightly branched monoolefins, the bulk dehydrogenated product stream may contain, on average, fewer than 3, or between 3 and 3.4, primary carbon atoms per monoolefin molecule in the dehydrogenated product stream. Depending on the relative proportions of linear and lightly branched monoolefins, the dehydrogenated product stream, or the sum of all the monoolefins that pass to the alkylation zone, may have from 2.25 to 3.4 primary carbon atoms per monoolefin molecule.

Linear and/or nonlinear paraffins which pass to the alkylation section, via the dehydrogenated product stream, have a total number of carbon atoms per paraffin molecule of generally from about 8 to about 28, preferably from 8 to 15, and more preferably from 10 to 13 carbon atoms. The nonlinear paraffins in the dehydrogenated product stream may include lightly branched paraffins and may also include paraffins having at least one quaternary carbon atom. Such linear and nonlinear paraffins are expected to act as a diluent in the alkylation step and not to materially interfere with the alkylation step. However, the presence of such diluents in the alkylation reactor generally results in higher volumetric flow rates of process streams, and, in order to accommodate these higher flow rates, larger equipment in the alkylation reaction circuit (i.e., larger alkylation reactor and more alkylation catalyst), and larger product recovery facilities may be required.

Monoolefins that are more highly branched than the lightly branched monoolefins may also be present in the dehydrogenated product stream, but because on alkylation such highly branched monoolefins tend to form BAB, preferably their concentration in the dehydrogenated product stream is minimized. For example, the dehydrogenated product stream may contain monoolefin molecules consisting of at least one quaternary carbon atom, which tend on alkylation to form phenyl-alkanes that have in the aliphatic alkyl portion a quaternary carbon atom that is not bonded by a carbon-carbon bond with a carbon atom of the phenyl portion. Therefore, monoolefin molecules consisting of at least one quaternary carbon atom generally comprise less than 10 mol-%, preferably less than 5 mol-%, more preferably less than 2 mol-%, and most preferably less than 1 mol-% of the dehydrogenated product stream or of the sum of all the monoolefins that pass to the alkylation zone.

In the alkylation section, the monoolefins in the dehydrogenated product stream are reacted with a phenyl compound (i.e., an aromatic). In the general case, the monoolefins could be reacted with other phenyl compounds besides benzene, such as alkylated or otherwise substituted derivatives of benzene including toluene and ethylbenzene, but the product of such an alkylation may not be as suitable a detergent precursor as alkylated benzenes. But for detergent alkylation, the preferred phenyl compound is benzene. Although the stoichiometry of the alkylation reaction requires only 1 molar proportion of phenyl compound per mole of total monoolefins, the use of a 1:1 mole proportion results in excessive olefin polymerization and polyalkylation. That is, the reaction product under such conditions would consist not only of the desired monoalkylbenzenes, but also of large amounts of the dialkylbenzenes, trialkylbenzenes, possibly higher polyalkylated benzenes, olefin dimers, trimers, etc., and unreacted benzene. On the other hand, it is desired to have the phenyl compound:monoolefin molar ratio as close to 1:1 as possible to maximize utilization of the phenyl compound and to minimize the recycle of unreacted phenyl compound. The actual molar proportion of phenyl compound to total monoolefin will therefore have an important effect on both conversion and, perhaps more importantly, selectivity of the alkylation reaction. In order to carry out alkylation with the conversion and selectivity required using the catalysts of this invention's process, the total phenyl compound: monoolefin molar ratio may be generally from about 2.5:1 up to about 50:1 and normally from about 8:1 to about 35:1.

The phenyl compound and the monoolefins are reacted under alkylation conditions in the presence of a solid alkylation catalyst. These alkylation conditions include a temperature in the range between about 176° F. (80° C.) and about 437° F. (225° C.). Since the alkylation is conducted in at least partial liquid phase, and preferably in either an all-liquid phase or at supercritical conditions, pressures for this embodiment must be sufficient to maintain reactants in the liquid phase. The requisite pressure necessarily depends upon the olefin, the phenyl compound, and temperature, but normally is in the range of 200-1000 psi(g) (1379-6895 kPa(g)), and most usually 300-500 psi(g) (2069-3448 kPa(g)).

While the alkylation conditions are sufficient to alkylate the phenyl compound with the lightly branched monoolefin, it is believed that under alkylation conditions only minimal skeletal isomerization occurs to the monoolefins entering the alkylation section. As used herein, skeletal isomerization of an olefin under alkylation conditions means isomerization that occurs during alkylation and which changes the number of carbon atoms in the aliphatic alkenyl chain of the olefin, in the aliphatic alkyl chain of the phenyl-alkane product, or in any reaction intermediate that is formed or derived from the lightly branched monoolefin prior to the withdrawal of the phenyl-alkane product from the alkylation conditions. By minimal skeletal isomerization it is meant that generally less than 25 mol-%, and preferably less than 10 mol-%, of the olefin, the aliphatic alkyl chain, and any reaction intermediate undergoes skeletal isomerization. It is further believed that under alkylation conditions minimal skeletal isomerization occurs for any other olefins in the olefinic stream. Thus, alkylation preferably occurs in the substantial absence of skeletal isomerization of the lightly branched monoolefin, and the extent of light branching of the lightly branched monoolefin is identical to the extent of light branching in the aliphatic alkyl chain in the phenyl-alkane product molecule. Accordingly, the number of primary carbon atoms in the lightly branched monoolefin is preferably the same as the number of primary carbon atoms per phenyl-alkane molecule. Insofar as an additional methyl group branch does form on the aliphatic alkyl chain of the phenyl-alkane product, the number of primary carbon atoms in the phenyl-alkane product may be slightly higher the number of primary carbon atoms in the lightly branched monoolefin. Finally, although the formation of 1-phenyl-alkane product is not significant at alkylation conditions, insofar as a 1-phenyl-alkane molecule is formed by alkylating a phenyl compound with a lightly branched monoolefin having a primary carbon atom on each end of the aliphatic alkenyl chain, the number of primary carbon atoms in the phenyl-alkane product will be slightly less than the number of primary carbon atoms in the lightly branched monoolefin.

The alkylation of the phenyl compound with the lightly branched monoolefins produces $(m_t\text{-alkyl}_i)_i$-n-phenyl-alkanes, where the aliphatic alkyl group has two, three, or four primary carbon atoms per phenyl-alkane molecule. Preferably, the aliphatic alkyl group has three primary carbon atoms per phenyl-alkane molecule, and more preferably one of the three primary carbon atoms is in a methyl group at one end of the aliphatic alkyl chain, the second primary carbon atom is in a methyl group at the other end of the chain, and the third primary carbon atom is in a single methyl group branch attached to the chain. However, it is not necessary that all of the $(m_t\text{-alkyl}_i)_i$-n-phenyl-alkanes produced by the present invention have the same number of primary carbon atoms per phenyl-alkane molecule. Generally from about 0 mol-% to about 75 mol-%, and preferably from about 0 mol-% to about 50 mol-%, of the $(m_t\text{-alkyl}_i)_i$-n-phenyl-alkanes produced may have 2 primary carbon atoms per phenyl-alkane molecule. Generally, as many as possible, and typically from about 25 mol-% to about 100 mol-%, of the $(m_t\text{-alkyl}_i)_i$-n-phenyl-alkanes produced may have 3 primary carbon atoms per phenyl-alkane molecule. Generally from about 0 mol-% to about 40 mol-% of the $(m_t\text{-alkyl}_i)_i$-n-phenyl-alkanes produced may have 4 primary carbon atoms. Thus, (m-methyl)-n-phenyl-alkanes having only one methyl group branch are preferred and are referred to herein as monomethyl-phenyl-alkanes. It is expected that the number of primary, secondary, and tertiary carbon atoms per product phenyl-alkane molecule can be determined by high resolution multipulse nuclear magnetic resonance (NMR) spectrum editing and distortionless enhancement by polarization transfer (DEPT), which is described in the brochure entitled "High Resolution Multipulse NMR Spectrum Editing and DEPT," which is distributed by Bruker Instruments, Inc., Manning Park, Billerica, Mass., USA, and which is incorporated herein by reference.

The alkylation of the phenyl compound with the monoolefins and the product of that alkylation have a selectivity of 2-phenyl-alkanes of generally from about 40 to about 100 and preferably from about 60 to about 100 and in another embodiment from about 50 to about 100, and an internal quaternary phenyl-alkane selectivity of generally less than 10 and preferably less than 5 and in another embodiment less than about 8. Quaternary phenyl-alkanes can form by alkylating the phenyl compound with a lightly branched monoolefin having at least one tertiary carbon atom. A tertiary carbon atom is a carbon atom which, while also possibly bonded to other atoms besides carbon, is bonded to only three carbon atoms. If, on alkylation, a tertiary carbon atom of the monoolefin forms a carbon-carbon bond with one of the carbon atoms of the phenyl compound, that tertiary carbon atom becomes a quaternary carbon atom of the aliphatic alkyl chain. Depending on the location of the quaternary carbon atom with respect to the ends of the aliphatic alkyl chain, the resulting quaternary phenyl-alkane may be either an internal or an end quat.

The alkylation of the phenyl compound with the monoolefins has a selectivity to phenyl-alkanes having an aliphatic alkyl portion containing a quaternary carbon atom not bonded by a carbon-carbon bond with a carbon atom of the phenyl portion of less than 10, and preferably less than 1. A suitable approximation of the selectivity to such quaternary phenyl-alkanes can be arrived at by using the following formula:

$$T = 100\left(\frac{C_{QO}}{C_O}\right)$$

where
  T=selectivity to phenyl-alkanes having an aliphatic alkyl portion containing a quaternary carbon atom not bonded by a carbon-carbon bond with a carbon atom of the phenyl portion
  $C_{QO}$=moles of monoolefins having a quaternary carbon atom entering the selective alkylation zone
  $C_O$=moles of monoolefins entering the selective alkylation zone The values of $C_{QO}$ and $C_O$ can be determined using the molar flow rate of monoolefins entering the selective alkylation zone and the previously mentioned modified apparatus and method of Schulz et al. The selectivity, T, can be estimated using this formula if each monoolefin entering the selective alkylation zone has an equal probability of alkylating the phenyl compound, regardless of whether the monoolefin has a quaternary carbon atom. As a first approximation, this condition is met when more than about 40 wt-% of the monoolefins entering the selective alkylation zone are lightly branched monoolefins or normal monoolefins.

Alkylation of the phenyl compound by the monoolefins may be conducted either as a batch method or in a continuous manner, although the latter is greatly preferred and therefore will be described in some detail. The alkylation catalyst may be used as a packed bed or a fluidized bed. The dehydrogenated product stream to the alkylation reaction zone may be passed either upflow or downflow, or even horizontally as in a radial bed reactor. The admixture of benzene and the dehydrogenated product stream containing the lightly branched monoolefins is introduced at a total phenyl compound:monoolefin molar ratio of between 2.5:1 and 50:1, although usually the molar ratio is in the range between about 8:1 and 35:1. In one desirable variant, portions of the dehydrogenation product stream may be fed into several discrete points within the alkylation reaction zone, and at each zone the phenyl compound:monoolefin molar ratio may be greater than 50:1. However, the total benzene:olefin ratio used in the foregoing variant of this invention still will be within the stated range. The total combined feed, that is, phenyl compound plus dehydrogenated product stream containing lightly branched monoolefins, is passed through the packed bed at a liquid hourly space velocity (LHSV) between about 0.3 and about 6 $hr^{-1}$ depending upon alkylation temperature, how long the catalyst has been used, and so on. Lower values of LHSV within this range are preferred. The temperature in the alkylation reaction zone will be maintained at between about 80° C. and about 225° C. (176 to 437° F.), and pressures generally will vary between about 200 and about 1000 psi(g) (1379 to 6895 kPa(g)) to ensure a liquid phase or supercritical conditions. The alkylation reaction usually goes to at least about 98% conversion based on the monoolefin and therefore, little unreacted monoolefin is present in the alkylation reaction zone effluent.

Any suitable alkylation catalyst may be used in the present invention, provided that the requirements for conversion, selectivity, and activity are met. Preferred alkylation catalysts comprise zeolites having a zeolite structure type selected from the group consisting of BEA, MOR, MTW, and NES. Such zeolites include mordenite, ZSM-4, ZSM-12, ZSM-20, offretite, gmelinite, beta, NU-87, and gottardiite. These zeolite structure types, the term "zeolite structure type," and the term "isotypic framework structure" are used herein as they are defined and used in the *Atlas of Zeolite Structure Types*, by W. M. Meier, et al., published on behalf of the Structure Commission of the International Zeolite Association by Elsevier, Boston, Mass., USA, Fourth Revised Edition, 1996. Alkylations using NU-87 and NU-85, which is an intergrowth of zeolites EU-1 and NU-87, are described in U.S. Pat. Nos. 5,041,402 and 5,446,234, respectively. Gottardiite, which has an isotypic framework structure of the NES zeolite structure type, is described in the articles by A. Alberti et al., in Eur. J. Mineral., 8, 69-75 (1996), and by E. Galli et al., in Eur. J. Mineral., 8, 687-693 (1996). Most preferably, the alkylation catalyst comprises mordenite.

Useful zeolites for the alkylation catalyst in the present invention generally have at least 10 percent of the cationic sites thereof occupied by ions other than alkali or alkaline-earth metals. Such other ions include, but are not limited to hydrogen, ammonium, aluminum, rare earth, zinc, copper, and aluminum. Of this group, particular preference is accorded ammonium, hydrogen, rare earth, or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. In certain embodiments, the extent of replacement is such as to produce a zeolite material in which at least 50 percent of the cationic sites are occupied by hydrogen ions.

The zeolites may be subjected to various chemical treatments, including alumina extraction (dealumination) and combination with one or more metal components, such as the metals of Groups IIIB (IUPAC 3), IVB (IUPAC 4), VIB (IUPAC 6), VIIB (IUPAC 7), VII (IUPAC 8-10), and IIB (IUPAC 12). It is also contemplated that the zeolites may, in some instances, desirably be subjected to thermal treatment, including steaming or calcination in air, hydrogen, or an inert gas, e.g. nitrogen or helium. A suitable steaming treatment comprises contacting the zeolite with an atmosphere containing from about 5 to about 100% steam at a temperature of from about 250° C. (482° F.) to 1000° C. (1832° F.). Steaming may last for a period of between about 0.25 and about 100 hours and may be conducted at pressures ranging from subatmospheric to several hundred atmospheres.

It may be useful to incorporate the zeolites that are useful in this invention in another material, e.g., a matrix material or binder that is resistant to the temperature and other conditions used in the process. Suitable matrix materials include synthetic substances, naturally occurring substances, and inorganic materials such as clay, silica, and/or metal oxides. Matrix materials can be in the form of gels including mixtures of silica and metal oxides. Gels including mixtures of silica and metal oxides may be either naturally occurring or in the form of gels or gelatinous precipitates. Naturally occurring clays which can be composited with the zeolite used in this invention include those of the montmorillonite and kaolin families, which families include the sub-bentonites and the kaolins commonly known as Dixie, McNamee-Georgia, and Florida clays or others in which the main mineral constituent is halloysite, kaolinite, dickite, nacrite, or anauxite. Such clays can be used as a matrix material in their raw states as originally mined, or can be subjected to calcination, acid treatment or chemical modification prior to their use as matrix materials. In addition to the foregoing materials, the zeolite used in this invention may be compounded with a porous matrix material, such as alumina, silica-alumina, silica-magnesia, silica-zirconia, silica-thoria, silica-beryllia, silica-titania, and aluminum phosphate as well as ternary combinations, such as silica-alumina-thoria, silica-alumina-zirconia, silica-alumina-magnesia, and silica-magnesia-zirconia. The matrix material may be in the form of a cogel. The relative proportions of and matrix material may vary widely, with the zeolite content ranging generally from between about 1 and about 99% by weight, usually in the range of about 5 to about 80% by weight, and preferably in the range of about 30 to about 80% by weight, of the combined weight of zeolite and matrix material.

The zeolites that are useful in the alkylation catalyst generally have a framework silica:alumina molar ratio of from about 5:1 to about 100:1. When the zeolite of the alkylation catalyst is mordenite, the mordenite has a framework silica:alumina molar ratio generally of from about 12:1 to about 90:1, and preferably of from about 12:1 to about 25:1. As used herein, the term "framework silica:alumina molar ratio" means the molar ratio of silica per alumina, that is the molar ratio of $SiO_2$ per $Al_2O_3$, in the zeolite framework.

When zeolites have been prepared in the presence of organic cations they may not be sufficiently catalytically active for alkylation. Without being bound to any particular theory, it is believed that the insufficient catalytic activity is the result of the organic cations from the forming solution occupying the intracrystalline free space. Such catalysts may be activated, for example, by heating in an inert atmosphere at 540° C. (1004° F.) for one hour, ion exchanging with ammonium salts, and calcining at 540° C. (1004° F.) in air. A calcination temperature of higher than 540° C. (1004° F.) may be used to ensure decomposition of any ammonia on the catalyst. The presence of organic cations in the forming solution may be essential to forming particular zeolites. Some natural zeolites may sometimes be converted to zeolites of the desired type by various activation procedures and other treatments such as ion exchange, steaming, alumina extraction, and calcination. When synthesized in the alkali metal form, the zeolite is conveniently converted to the hydrogen form, generally by intermediate formation of the ammonium form as a result of ammonium ion exchange and calcination of the ammonium form to yield the hydrogen form. Although the hydrogen form of the zeolite catalyzes the reaction successfully, the zeolite may also be partly in the alkali metal form.

The alkylation reaction zone produces an alkylation reaction effluent that enters separation facilities for the recovery of products and recyclable feed compounds. The alkylation reaction effluent passes into a benzene column which produces an overhead stream containing benzene which is recycled to the alkylation reaction zone and a bottoms stream containing the phenyl-alkane product. This bottoms stream passes into a paraffin column which produces an overhead stream containing unreacted paraffins and a bottoms stream containing the product phenyl-alkanes and any higher molecular weight by-product hydrocarbons formed in the alkylation reaction zone. The paraffin column bottoms stream may pass to a rerun column which produces an overhead phenyl-alkane product stream containing the MAB and a rerun column bottoms stream containing polymerized olefins and polyalkylated benzenes (heavy alkylate). Alternatively, if the heavy alkylate content of the paraffin column bottoms stream is sufficiently low, a rerun column is not necessary and the paraffin column bottoms stream may be recovered as the net MAB stream, which may be subsequently sulfonated to produce MABS.

Several variants of the subject process are possible. One variant includes the selective hydrogenation of diolefins that may be present in the dehydrogenated product stream, since diolefins may be formed during the catalytic dehydrogenation of paraffins. Selective diolefin hydrogenation converts the diolefins to monoolefins, which are the desired product of the dehydrogenation section, and produces a selective diolefin hydrogenation product stream. The selective diolefin hydrogenation product stream has a lower concentration of diolefins than the dehydrogenated product stream.

Another variant of the subject process includes selective removal of aromatic by-products that may be present in the dehydrogenated product stream. Aromatics may be present in the extract stream of the adsorptive separation section or aromatic by-products may be formed during the catalytic dehydrogenation of paraffins, and in either case these aromatics may cause a number of deleterious effects, such as deactivation of the catalyst in the alkylation section, decreasing the selectivity to the desired phenyl-alkanes, and accumulation to unacceptable concentration in the process. Suitable aromatics removal zones include sorptive separation zones containing a sorbent such as a molecular sieve and in particular 13X zeolite (sodium zeolite X), and liquid-liquid extraction zones. Selective removal of these aromatic by-products may be accomplished in one or more locations of the subject process. The aromatic by-products may be selectively removed from, for example, the extract stream, the dehydrogenated product steam, or the overhead liquid stream of the paraffin column that is recycled to the adsorptive separation zone or the dehydrogenation zone. Where the subject process includes a selective diolefin hydrogenation zone the aromatic byproducts may be selectively removed from the selective diolefin hydrogenation product stream. The selective aromatics removal zone produces a stream that has a decreased concentration of aromatic by-products than that of the stream passed to the selective aromatics removal zone. Detailed information on selective removal of aromatic by-products from an alkylaromatic process for the production of linear alkylbenzenes is disclosed in U.S. Pat. No. 5,276,231, the teachings of which are incorporated herein by reference. It is believed that a person of ordinary skill in the art is capable of modifying the teachings of U.S. Pat. No. 5,276,231 with respect to aromatic by-products removal, including choice of sorbent, operating conditions, and location in the process, so as to successfully remove aromatic by-products from a process for the production of MAB.

Although the selective removal of these aromatic by-products is preferably accomplished on a continuous basis, selective removal may also be done intermittently or on a batch-wise basis. Intermittent or batch-wise removal would be most useful when the capacity of the removal zone to remove the aromatic by-products from the process exceeds the rate at which aromatic by-products accumulate in the process. If, in addition, some variation in the level or concentration of aromatic by-products within the process is acceptable or tolerable, then the aromatic by-products selective removal zone could be placed on-stream in one of the above mentioned locations for a specified period of time until the concentration or level of aromatic by-products in the process is decreased to a sufficient minimum concentration. Then the aromatic by-products selective removal zone could be taken off-stream or bypassed until the concentration increases to the tolerable maximum concentration, at which time the removal zone could be placed on-stream again.

In a preferred embodiment of the process aspect of this invention, this invention is a process for producing a preferred MAB composition comprising phenyl-alkanes having one phenyl group and one aliphatic alkyl group, wherein the phenyl-alkanes have:

(i) an average weight of the aliphatic alkyl groups of the phenyl-alkanes of between the weight of a $C_{10}$ aliphatic alkyl group and a $C_{13}$ aliphatic alkyl group;

(ii) a content of phenyl-alkanes having the phenyl group attached to the 2- and/or 3-position of the aliphatic alkyl group of greater than 55 wt-% of the phenyl-alkanes; and (iii) an average level of branching of the aliphatic alkyl groups of the phenyl-alkanes of from 0.25 to 1.3 alkyl group branches per phenyl-alkane molecule when the sum of the contents of 2-phenyl-alkanes and 3-phenyl-alkanes is more than 55 wt-% and less than or equal to 85 wt-% of the phenyl-alkanes, or an average level of branching of the aliphatic alkyl groups of the phenyl-alkanes of from 0.4 to 1.3 alkyl group branches per phenyl-alkane molecule when the sum of the concentrations of 2-phenyl-alkanes and the 3-phenyl-alkanes is greater than 85 wt-% of the phenyl-alkanes; and (iv) wherein the aliphatic alkyl groups of the phenyl-alkanes comprise primarily linear aliphatic alkyl groups and mono-branched aliphatic alkyl groups, and wherein the alkyl group branches on the aliphatic alkyl chain of the aliphatic alkyl groups comprise primarily small substituents, such as methyl group branches, ethyl group branches, or propyl group branches, and wherein the alkyl group branches attach to any position on the aliphatic alkyl chain of the aliphatic alkyl groups provided that phenyl-alkanes having at least one quaternary carbon atom on the aliphatic alkyl group comprise less than 20% of the phenyl-alkanes.

One process for producing this preferred MAB composition comprises separating by adsorptive separation paraffins having an average weight between the weight of a $C_{10}$ paraffin and a $C_{13}$ paraffin to produce extract paraffins having an average level of branching of from 0.25 to 1.3, or of from 0.4 to 1.3, alkyl group branches per paraffin molecule. These extract paraffins primarily comprise linear paraffins and mono-branched paraffins, and the alkyl group branches on the aliphatic alkyl chain of the extract paraffins primarily comprise small substituents, such as methyl group branches, ethyl group branches, or propyl group branches. The alkyl group branches of the extract paraffins may be attached to any position on the aliphatic alkyl chain of the paraffin, subject to certain limitations that depend on the desired characteristics of the resultant phenyl-alkanes. The extract paraffins are dehydrogenated to produce the corresponding mono-olefins, which alkylate a phenyl compound to produce phenyl-alkanes. The resultant phenyl-alkanes have the characteristics that the phenyl-alkanes having the phenyl group attached to the 2- and/or 3-position of the aliphatic alkyl group comprise greater than 55 wt-% of the phenyl-alkanes, and the phenyl-alkanes having at least one quaternary carbon atom on the aliphatic alkyl group comprise less than 20% of the phenyl-alkanes.

Sulfonation of the phenyl-alkanes produced by the processes of this invention can be accomplished by contacting the phenyl-alkane compounds with any of the well-known sulfonation systems, including those described in *Detergent Manufacture Including Zeolite Builders and Other New Materials*, by Marshall Sittig, Noyes Data Corporation, Park Ridge, N.J., 1979, and in Volume 56 of "Surfactant Science" series, Marcel Dekker, Inc., New York, N.Y., 1996. Sulfonation of the phenyl-alkane compounds produces a sulfonated product comprising phenyl-alkane sulfonic acids. Common sulfonation systems employ sulfonating agents such as sulfuric acid, chlorosulfonic acid, oleum, and sulfur trioxide. Sulfonation using a mixture of sulfur trioxide and air is described in U.S. Pat. No. 3,427,342.

After sulfonation, the sulfonated product can be neutralized by contact with any suitable alkali, such as sodium, potassium, ammonium, magnesium, calcium, and substituted ammonium alkalis, and mixtures thereof. Neutralization of the phenyl-alkane sulfonic acids produces a neutralized product comprising phenyl-alkane sulfonates. Suitable neutralizing agents include sodium hydroxide, potassium hydroxide, ammonium hydroxide, sodium carbonate, sodium bicarbonate, potassium carbonate, magnesium hydroxide, magnesium carbonate, basic magnesium carbonate (magnesia alba), calcium hydroxide, and calcium carbonate, and mixtures thereof.

In other aspects of the present invention, this invention is the MAB compositions and the MABS compositions produced by the processes disclosed herein.

In yet another aspect of the present invention, this invention is the use of the MAB compositions produced by the processes disclosed herein as lubricants. These phenyl-alkanes are believed to have properties of viscosity, temperature-dependence of viscosity, and density that make them advantageous for use as petroleum lubricants. The use of phenyl-alkanes as lubricants is described, for example, in the article by E. R. Booser in *Kirk-Othmer Encyclopedia of Chemical Technology*, Fourth Edition, Volume 15, John Wiley and Sons, New York, N.Y., USA, 1995, pp. 463-517, to which reference is made for a description of such lubricants and their use.

In still another aspect, this invention is the use of the MABS compositions produced by the processes disclosed herein as lubricant additives. It is believed that phenyl-alkane sulfonates, either in the form of normal salts or basic salts of phenyl-alkane sulfonic acids, produced as disclosed herein, have the ability to reduce or prevent deposits in engines operating at high temperatures. As used herein, the term "normal salt" of an acid means a salt which contains the stoichiometric amount of metal required for the neutralization of the acidic group or groups present, and the term "basic salt" means a salt which contains more metal than is required for the neutralization reaction. The excess metal in the form of basic salts is believed to be capable of neutralizing oil oxidation combustion products and "blow-by" fuel combustion products. Phenyl-alkane sulfonates and their use as lubricant additives, in particular as detergents, is described, for example, in the above-mentioned Booser article; in *Lubricant Additives*, by C. V. Smalheer and R. K. Smith, The Lezius-Hiles Co., Cleveland, Ohio, USA, 1967, pp. 2-3; and in the article by R. W. Watson and T. F. McDonnell, Jr., entitled "Additives—The Right Stuff for Automotive Engine Oils," in *Fuels and Lubricants Technology: An Overview SP-603*, Society of Automotive Engineers, Warrendale, Pa., USA, October 1984, pp. 17-28.

A complete operation of the process aspect of this invention can be more fully understood from a process flow for a preferred embodiment of this invention. The drawing shows a preferred arrangement for an integrated separation-dehydrogenation-alkylation scheme of this invention. The following description of the drawing is not meant to preclude other arrangements for the process flow of this invention and is not intended to limit this invention as set forth in the claims.

Referring now to the drawing, a feed mixture comprising an admixture of $C_{10}$-$C_{13}$, including lightly branched paraffins, more highly branched paraffins, and normal (non-branched) paraffins, is charged via a line 12 to an adsorptive separation zone 20 which employs normal paraffin, cycloparaffin, and/or isooctane as the desorbent. A raffinate stream comprising more highly branched paraffins and a cycloparaffin or isooctane is removed from the adsorptive separation zone 20 in a line 24 and passes to a raffinate column 30. The raffinate column 30 operates at conditions to produce an overhead stream comprising normal paraffin, cycloparaffin, and/or isooctane in line 32 and a bottom stream comprising more highly branched paraffins in a line 28. An extract stream comprising lightly branched paraffins, normal paraffins, and a cycloparaffin or isooctane is removed from adsorptive separation zone 20 in line 34 and passes to an extract column 40. The extract column 40 operates at conditions to produce an overhead stream comprising normal paraffin, cycloparaffin, and/or isooctane in line 46. The overhead streams in lines 32 and 46 are combined to form a desorbent stream which is recycled to the adsorptive separation zone in a line 44. The extract column 40 also produces a bottom stream comprising lightly branched paraffins and normal paraffins in a line 52.

The bottom stream removed from the extract column 40 passes through line 52 and is admixed with recycled hydrogen from a line 82 to form a mixture of paraffins and hydrogen that flows through a line 56. The mixture of paraffins and hydrogen flowing through the line 56 is first heated in an indirect heat exchanger 58 and then passes through a line 62 to a fired heater 60. The mixture of hydrogen and paraffins that is withdrawn from the fired heater 60 passes through a line 64 into a dehydrogenation reactor 70. Inside the dehydrogenation reactor 70, the paraffins contact a dehydrogenation catalyst at conditions which effect the conversion of a significant amount of the paraffins to the corresponding olefins. There is thus produced a dehydrogenation reactor effluent stream carried by line 66 which comprises a mixture of hydrogen, paraffins, monoolefins including lightly branched monoolefins, diolefins, $C_9$-minus hydrocarbons, and aromatic hydrocarbons. This dehydrogenation reactor effluent stream is first cooled by indirect heat exchange in the heat exchanger 58, passes through a line 68, and is then further cooled in an indirect heat exchanger 72. This cooling is sufficient to condense substantially all of the $C_4$-plus hydrocarbons into a liquid phase stream and separate the liquid phase stream from the remaining hydrogen-rich vapor. This dehydrogenation reactor effluent stream flows through a line 74 and enters the vapor-liquid separation vessel 80. In the separation vessel 80, the dehydrogenation reactor effluent stream is divided into a hydrogen-rich vapor phase stream removed through a line 76 and a dehydrogenation product stream removed through a line 84. The vapor phase stream is divided into a net hydrogen product stream removed through a line 78 and the hydrogen-containing stream that is recycled by the line 82.

The dehydrogenated product stream removed from the bottom of the separation vessel 80 contains normal paraffins, lightly branched paraffins, normal monoolefins, lightly branched monoolefins, $C_9$-minus hydrocarbons, diolefins, aromatic by-products, and some dissolved hydrogen. The dehydrogenated product stream, which is the liquid phase effluent of the separator vessel 80, is then passed through a line 84 to a selective hydrogenation reactor 86. Inside the selective hydrogenation reactor 86, the dehydrogenated product stream is contacted in the presence of a selective hydrogenation catalyst at conditions which effect the conversion of a significant amount of the diolefins to the corresponding monoolefins. This conversion by hydrogenation can be effected using the dissolved hydrogen in the dehydrogenated product stream and/or additional make-up hydrogen (not shown) charged to the selective hydrogenation reactor. There is thus produced a selective hydrogenation reactor effluent stream carried by a line 88, which comprises a mixture of hydrogen, normal paraffins, lightly paraffins, normal monoolefins, lightly branched monoolefins, $C_9$-minus hydrocarbons, and aromatic by-product hydrocarbons. This selective hydrogenation reactor effluent is then passed through the line 88 to a stripping column 90. In this stripping column, the $C_9$-minus hydrocarbons produced in the dehydrogenation reactor as by-products and any remaining dissolved hydrogen are separated from the $C_{10}$-plus hydrocarbons and concentrated into a net overhead stream removed from the process through a line 94.

The remainder of the hydrocarbons entering the stripping column 90 are concentrated into a stripping effluent stream carried by a line 96. The stripping effluent stream is then passed into an aromatics removal zone 100. In this zone, the stripping effluent stream is contacted with an adsorbent under conditions which promote the removal of the aromatic by-products. The effluent from the aromatics removal zone 100 is transferred via a line 98. This stream comprises an admixture of the normal paraffins, lightly branched paraffins, normal monoolefins, and lightly branched monoolefins, and has a greatly reduced concentration of aromatic by-products compared to the stripping effluent stream. This admixture is combined with benzene from a line 112 and passed via a line 102 into an alkylation reactor 104. In the alkylation reactor, benzene and the monoolefins are contacted with an alkylation catalyst at alkylation-promoting conditions to produce phenyl-alkanes.

The alkylation reactor effluent stream is carried by a line 106 and passes into a benzene fractionation column 110 by a line 106. This stream comprises an admixture of benzene, normal paraffins, lightly branched paraffins, phenyl-alkanes comprising one phenyl portion and one aliphatic alkyl portion having 1 or 2 primary carbon atoms, and phenyl-alkanes comprising one aliphatic alkyl portion and one phenyl portion where the aliphatic alkyl portion has 2, 3, or 4 primary carbon atoms and has no quaternary carbon atoms except for any quaternary carbon atom bonded to the phenyl portion. In other words, this stream comprises an admixture of benzene, normal paraffins, lightly branched paraffins, and MAB. This stream is separated in benzene fractionation column 110 into a bottom stream and an overhead stream comprising benzene and possibly light gases. The overhead stream is carried by a line 107 and combines with make-up benzene charged to a line 109. The combined stream flows through a line 108 to a separator drum 120 from which noncondensed light gases, if any, are removed via a line 114 and condensed liquid is withdrawn by a line 116 to supply reflux to column 110 via a line 118 and benzene for recycle by a line 112. A line 122 carries the remainder of the alkylation effluent stream from column 110 to a paraffin column 124 from which an overhead stream containing a mixture of paraffins and generally less then 0.3 wt-% monoolefins is taken. A paraffin column bottom stream containing the phenyl-alkanes and heavy alkylate by-products is taken by a line 126. The contents of line 126 are separated in a rerun column 130 into a bottom stream 132 comprising heavy alkylate and an overhead alkylate product stream 128 containing the phenyl-alkane compounds. Sulfonation of the phenyl-alkane compounds in the overhead alkylate product stream 128 can be accomplished to produce phenyl-alkane sulfonic acids, which can be neutralized.

The following examples are presented to illustrate this invention and are not intended as undue limitations in the generally broad scope of the invention as set forth in the claims.

EXAMPLE 1

A "pulse test" procedure may be employed to test adsorbents with a particular feed mixture and desorbent material to measure such adsorbent characteristics as adsorptive capacity, selectivity, resolution and exchange rate. The basic pulse test apparatus consists of a tubular adsorbent chamber of approximately 70 cc volume having an inlet and outlet at opposite ends of the chamber. The chamber is contained within a temperature control means and pressure control equipment is used to maintain the chamber at a constant predetermined pressure. Quantitative and qualitative analytical equipment such as refractometers, polarimeters and chromatographs can be attached to an outlet line of the chamber and used to detect quantitatively and/or determine qualitatively one or more components in the effluent stream leaving the adsorbent chamber. During a pulse test, the adsorbent is first filled to equilibrium with a particular desorbent material by passing the desorbent material through the adsorbent chamber. A pulse of the feed mixture, sometimes diluted in desorbent, is then injected for a duration of one or more minutes. Desorbent flow is resumed, and the feed mixture components are eluted as in a liquid-solid chromatographic operation. The effluent can be analyzed on-stream. Alternatively, or in addition effluent fractions can be collected and later analyzed separately. Traces of the envelopes of corresponding component peaks can then be plotted in terms of component concentration versus quantity of effluent. The large number of hydrocarbons in the feed stream of the subject tests makes this impractical.

From information derived from the pulse test the adsorbent/desorbent system performance can normally be rated in terms of retention volume for an extract or a raffinate component, selectivity for one component with respect to the other, stage time, the resolution between the components and the rate of desorption of an extract component by the desorbent. The retention volume of an extract or a raffinate component may be determined from the distance between the center of the peak envelope of an extract or a raffinate component and the peak envelope of a tracer component or some other known reference point. It is expressed in terms of the volume in cubic centimeters of desorbent pumped during the time interval corresponding to the distance between the peak envelopes.

Table 1 lists variables and results of small scale "pulse tests" performed to evaluate various desorbents and conditions on several feed mixtures. The materials labeled Raffinate A and B are the raffinate streams of commercial adsorptive separation units which recover normal paraffins from a $C_{10}$-$C_{14}$ hydrocarbon fraction. The desorbent column in Table 1 indicates the volume percent of each component of the desorbent as specified by the footnotes.

TABLE 1

| Run No. | Feed Mixture | Temp, ° C. | Desorbent* |
|---|---|---|---|
| 9577-77 | Raffinate A | 150 | 50 C5/50 N6 |
| 9577-85 | Raffinate A | 100 | 50 C5/50 N6 |
| 9937-01 | Raffinate A | 150 | 100 C6 |
| 9937-06 | Raffinate A | 150 | 70 C6/30 N6 |
| 9937-17 | Raffinate A | 150 | 50 C6/50 N6 |
| 9937-25 | Raffinate B | 150 | 50 C6/50 N6 |
| 9953-06 | Kerosene | 150 | 50 C6/50 N6 |

*C5 indicates cyclopentane C6 indicates cyclohexane N6 indicates n-hexane

An adsorbent comprising 80% silicalite and 20% silica binder was used in all tests. The tests were performed in a chromatographic column having an adsorbent volume of 70 ml. The flow rate through the column was 1.21 cc/min.

The very large number of different compounds in the feed mixture pulse, including several different monomethyl paraffins and the limitations inherent in the simple pulse test procedure results in the test results differing from those often reported with this test procedure for other separations. In these other separations, the feed mixture may contain two to four components if specific isomers such as the xylenes are being separated. A plot of an analysis of the effluent of the pulse test will then often show slightly overlapping peaks for the different components. With the high number of compounds involved in the subject separation such resolution is not reasonably possible. The effectiveness of the separation was therefore determined by collecting fractions of the effluent and analyzing each fraction. A new fraction was taken every two minutes. The initial fractions had high concentrations of desorbent and were followed by fractions having high concentrations of the more highly branched nonnormal hydrocarbons. The desired acyclic hydrocarbons having only 3 primary carbon atoms (i.e., monomethyl hydrocarbons) tended to be concentrated in the fractions collected at the end of the pulse of feed mixture components. Table 2 gives the concentration (wt percent) of acyclic paraffins having only 3 primary carbon atoms (i.e., monomethyl paraffins) present in several different fractions of Run No. 9937-07.

TABLE 2

| Fraction No. | Acyclic Paraffins Having Only 3 Primary Carbon Atoms, % |
|---|---|
| 18 | 34 |
| 19 | 48 |
| 20 | 60 |
| 22 | 55 |
| 24 | 60 |
| 26 | 77 |
| 28 | 77 |
| 32 | 79 |
| 38 | 96 |

For Run No 9937-06, liquid collected as fractions No. 19 to 100 was combined. The combined liquid was analyzed and found to contain the weight percentages of different structural classes of compounds on a desorbent free basis as shown in Table 3.

TABLE 3

| acyclic paraffins having only 3 primary carbon atoms (monomethyl branched) | 64% |
|---|---|
| acyclic paraffins having only 4 primary carbon atoms (dimethyl branched) | 2.7% |
| acyclic paraffins having only 2 primary carbon atoms (normal paraffins) | 4.6% |
| aromatics | 4.1% |
| naphthenes | 13.9% |
| unknowns | 10.7% |

For Run No. 9937-17, liquid collected as fractions No. 23 to 50 was combined. The combined liquid was analyzed and found to contain the weight percentages of different structural classes of compounds, as shown in Table 4:

TABLE 4

| acyclic paraffins having only 3 primary carbon atoms (monomethyl branched) | 77% |
|---|---|
| acyclic paraffins having only 4 primary carbon atoms (dimethyl branched) | 0.1% |
| acyclic paraffins having only 2 primary carbon atoms (normal) | 9.6% |
| aromatics | 4.1% |
| naphthenes | 3.8% |
| unknowns | 4.8% |

A sample formed by combining liquid from fractions 23 to 48 of Run 9953-6 was analyzed and found to contain 67% acyclic paraffins having only 3 primary carbon atoms (i.e., monomethyl branched compounds) and 9.3% acyclic paraffins having only 2 primary carbon atoms (i.e., normal paraffins).

In comparing this data to the performance which is normally desired in commercial separations it must be noted that the data is derived from screening tests used to compare the performance of different desorbent/adsorbent pairs or operating conditions. Better results in terms of selectivity will result from optimization in terms of adsorbent composition, desorbent composition and operating conditions. Further the use of simulated moving bed (SMB) technology or even better batch separation technology will improve the performance of the process.

EXAMPLE 2

In this example, a representative mixture of $C_{10}$ pure components was subjected to a pulse test procedure with the use of a pre-pulse of $C_8$ isoparaffin. In the test, the feed mixture was a mixture containing equal volumes of 3,3,5-trimethylheptane, 2,6-dimethyloctane, 2-methylnonane, normal decane, and 1,3,5-trimethylbenzene. The pulse test column had a volume of 70 cc and was held at a temperature of 120° C. (248° F.). The flow rate through the column was 1.1 cc/min. The adsorbent was silicalite and the desorbent was a 70/30 volume % mixture of normal heptane and isooctane. The test was run with a pre-pulse of 40 ml of isooctane injected into the test loop immediately before the feed mixture was injected.

Figure 2:
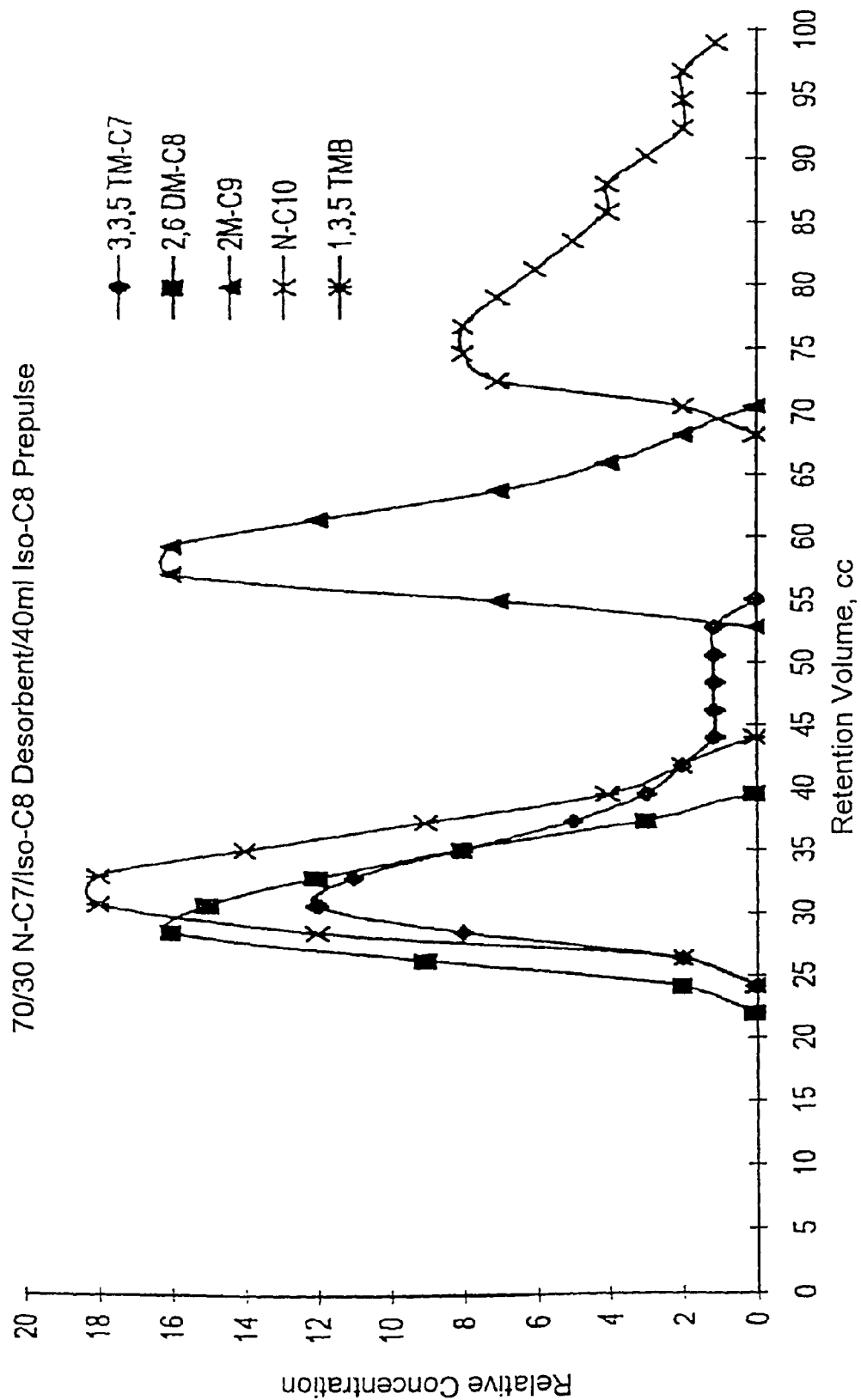
FIG. 2 shows a concentration profile of a pulse test separation of several $C_{10}$ compounds.

A graphical representation of the results of this test run is shown as FIG. 2. FIG. 2 shows a plot of the relative concentrations of the components versus time, as measured by the volume of collected effluent. FIG. 2 shows a useful separation between the monomethyl paraffin and the normal paraffin on the one hand and the di- and tri-methyl paraffins on the other hand. Although the use of the pre-pulse is believed to improve the separation of the monomethyl paraffin band in the effluent, it is believed that a useful separate band of the monomethyl paraffin is produced as a result of the presence of isooctane in the desorbent, even in the absence of a pre-pulse.

EXAMPLE 3

An olefinic stream comprising a blend of monomethyl $C_{12}$ olefins and having the composition shown in Table 5 was used.

TABLE 5

Composition of Olefinic Stream

| Olefin Component | Content (wt-%) |
|---|---|
| Lights[1] | 0.64 |
| Linear olefins[2] | 30.11 |
| 6-methyl undecene | 7.66 |
| 5-methyl undecene | 15.33 |
| 4-methyl undecene | 11.82 |
| 3-methyl undecene | 12.95 |
| 2-methyl undecene | 8.87 |
| Other alkyl olefins[3] | 9.05 |
| Heavies[4] | 3.53 |
| Total | 100 |

[1]Lights include olefins having fewer than 12 carbon atoms.
[2]Linear olefins include $C_{12}$ linear olefins.
[3]Other alkyl olefins include dimethyl, trimethyl, and other $C_{12}$ olefins
[4]Heavies include $C_{12}$ olefin dimers and trimers.

The olefinic stream was mixed with benzene to produce a combined stream consisting of 93.3 wt-% benzene and 6.7 wt-% olefinic stream, which corresponds to a molar ratio of benzene per olefin of about 30:1. A cylindrical reactor, which has an inside diameter of 0.875 in (22.2 mm), was loaded with 75 cc (53.0 g) of a mordenite-alumina extruded catalyst prepared from the hydrogen form of a mordenite having a $SiO_2/Al_2O_3$ of 18.

The combined stream was passed to the reactor and contacted the extrudate at a LHSV of 2.0 $hr^{-1}$, a total pressure of 500 psi(g) (3447 kPa(g)), and a reactor inlet temperature of 125° C. (257° F.). At these conditions, the reactor lined out over a period of 24 hours and then a selective liquid product was collected over the period of the next 6 hours.

The selective liquid product was analyzed by $^{13}C$ nuclear magnetic resonance (NMR) in order to determine the selectivity to 2-phenyl-alkanes and end quaternary phenyl-alkanes. The NMR analytical method typically consists of the following. A 0.5 g sample of phenyl-alkane mixture is diluted to 1.5 g with anhydrous deuterated chloroform. A 0.3 milliliter aliquot of the diluted phenyl-alkane mixture is mixed with 0.3 milliliter of 0.1 M chromium (III) acetylacetonate in deuterated chloroform in a 5 mm NMR tube. A small amount of tetramethylsilane (TMS) is added to the mixture as a 0.0 ppm chemical shift reference. The spectrum is run on a Bruker ACP-300 FT-NMR spectrometer, which is available from Bruker Instruments, Inc., Billerica, Mass., USA. The carbon spectrum is run at a field strength of 7.05 Tesla or 75.469 MHz in a 5 mm QNP probe with a sweep width of 22727 Hz (301.1 ppm) and about 65000 data points are collected. The quantitative carbon spectrum is obtained using gated on-acquisition $^1H$ decoupling (inverse gated decoupling). The quantitative $^{13}C$ spectrum is run with 7.99 microsecond (90°) pulses, 1.442 second acquisition time, a 5 second delay between pulses, a decoupler power, using composite pulse decoupling (CPD), of 18H with a pulse width of 105 microseconds (90°) and at least 2880 scans. The number of scans used depends on whether benzene is stripped from the liquid product prior to taking the above-mentioned 0.5 g sample. The data processing is done with the Bruker PC software WINNMR-1D, Version 6.0, which is also available from Bruker Instruments, Inc. During data processing a line broadening of 1 Hz is applied to the data. Specific peaks are integrated in the region between 152 ppm and 142 ppm. The $^{13}C$ NMR peak identifications of the chemical shifts of the benzylic carbon of the phenyl-alkane isomers is shown in Table 6. As used herein, the term "benzylic carbon" means the carbon in the ring of the phenyl group that is bound to the aliphatic alkyl group.

TABLE 6

$^{13}C$ NMR Peak Identifications

| Chemical Shift of the Benzylic Carbon (ppm) | Phenyl-alkane Isomer | Type of Quat[1] |
|---|---|---|
| 149.6 | 2-methyl-2-phenyl | End |
| 148.3 | 4-methyl-2-phenyl | NQ |
|  | m-methyl-m-phenyl, m > 3 | Internal |
| 148.0 | 5-methyl-2-phenyl | NQ |
| 147.8 | m-methyl-2-phenyl, m > 5 | NQ |
|  | 5-methyl-2-phenyl | NQ |
|  | 2-phenyl (linear) | NQ |
|  | 3-methyl-3-phenyl | Internal |
| 147.6 | 4-methyl-2-phenyl | NQ |
| 147.2 | 3-methyl-2-phenyl | NQ |
| 146.6 | 3-methyl-2-phenyl | NQ |
| 146.2-146.3 | m-methyl-4-phenyl, m ≠ 4 | NQ |
| 145.9-146.2 | m-methyl-3-phenyl, m > 5 | NQ |
| 145.9 | 3-phenyl (linear) | NQ |

[1]NQ = Nonquat

The peak at 148.3 ppm is identified both with 4-methyl-2-phenyl-alkanes and with m-methyl-m-phenyl-alkanes (m>3). However, when the m-methyl-m-phenyl-alkanes (m>3) are present at more than 1%, they are seen as a distinct peak at 0.03 ppm upfield of the peak for the 4-methyl-2-phenyl-alkanes. The peak at 147.8 ppm is considered herein to be identified with the 2-phenyl-alkanes as shown in Table 6, with possible interference from 3-methyl-3-phenyl-alkanes.

The end quaternary phenyl-alkane selectivity is computed by dividing the integral of the peak at 149.6 ppm by the sum of the integrals of all of the peaks listed in Table 6, and multiplying by 100. The 2-phenyl-alkane selectivity can be estimated if the amount of internal quaternary phenyl-alkanes contributing to the peaks at 148.3 ppm and 147.8 ppm is less than about 2%, as determined by the hereinafter-described gas chromatography/mass spectrometry method. As a first approximation, this condition is met when the sum of the integrals of the 4-phenyl-alkane and 3-phenyl-alkane peaks at 146.2-146.3 ppm and 145.9-146.2 ppm (respectively) is small relative to the sum of the integrals of all the peaks from 145.9 ppm to 149.6 ppm and the end quaternary phenyl-alkane selectivity is less than 10. When this is the case, the 2-phenyl-alkane selectivity is computed by dividing the sum of integrals of the peaks from 149.6 to 146.6 ppm by the sum of the integrals of all of the peaks listed in Table 6, and multiplying by 100.

The selective liquid product is also analyzed by gas chromatography/mass spectrometry in order to determine the selectivity to internal quaternary phenyl-alkanes. The gas chromatography/mass spectrometry analytical method typically consists of the following. The selective liquid product is analyzed by an HP 5890 Series II gas chromatograph (GC) equipped with an HP 7673 autosampler and an HP 5972 mass spectrometer (MS) detector. An HP Chemstation was used to control the data acquisition and analysis. The HP 5890 Series II, HP 7673, HP 5972, and HP Chemstation, or suitable equivalent hardware and software, are available from Hewlett Packard Company, Palo Alto, Calif., USA. The GC is equipped with a 30 meter×0.25 mm DB1HT(df=0.1 μm) column or equivalent, which can be obtained from J&W Scientific Incorporated, 91 Blue Ravine Road, Folsom, Calif., USA. Helium carrier gas at 15 psi(g) (103 kPa(g)) and 70° C. (158° F.) is used in constant pressure mode. The injector temperature is held at 275° C. (527° F.). The transfer line and MS source temperatures are held at 250° C. (482° F.). An oven temperature program of 70° C. (158° F.) for 1 minute, then to 180° C. (356° F.) at 1° C. per minute (1.8° F. per minute), then to 275° C. (527° F.) at 10° C. per minute (18° F. per minute), then hold at 275° C. (527° F.) for 5 minutes is used. The MS is tuned by the HP Chemstation software with the software set to standard spectra autotune. The MS detector is scanned from 50-550 Da with a threshold=50.

The concentrations of internal quaternary phenyl-alkanes in the selective liquid product are determined (i.e., the selective liquid product is quantitated) using the method of standard addition. Background information on standard addition methods can be found in Chapter 7 of the book entitled, *Samples and Standards*, by B. W. Woodget et al., published on behalf of ACOL, London by John Wiley and Sons, New York, in 1987.

First, a stock solution of internal quaternary phenyl-alkanes is prepared and quantitated using the following procedure. Benzene is alkylated with a monomethyl alkene using a nonselective catalyst such as aluminum chloride. The nonselective liquid product of this alkylation contains a blend of internal quaternary phenyl-alkanes and is referred to as the stock solution of internal quaternary phenyl-alkanes. Using standard GC methodology, the largest peaks corresponding to internal quaternary phenyl-alkanes in the stock solution are identified, and the concentrations of the internal quaternary phenyl-alkanes in the stock solution are determined (i.e., the stock solution is quantitated) using a flame ionization detector (FID). The retention times of the peaks for the internal quaternary phenyl-alkanes decrease as the index m in the formula m-methyl-m-phenyl-alkane increases and as the number of carbon atoms in the aliphatic alkyl group of the internal quaternary phenyl-alkane decreases. The concentration of each internal quaternary phenyl-alkane is computed by dividing the area of the peak of that internal quaternary phenyl-alkane by the sum of the areas of all of the peaks.

Next, a spiking solution of internal quaternary phenyl-alkanes is prepared in the following manner. An aliquot portion of the stock solution is diluted with dichloromethane (methylene chloride) to attain a nominal concentration of 100 wppm of one particular internal quaternary phenyl-alkane of interest (e.g., 3-methyl-3-phenyl decane). The solution that results is referred to as the spiking solution of internal quaternary phenyl-alkanes. The concentration of any other particular internal quaternary phenyl-alkane in the spiking solution may be greater or less than 100 wppm, depending on the concentration of that internal quaternary phenyl-alkane in the stock solution.

Third, a sample solution is prepared as follows. A weight of 0.05 g of an aliquot portion of the selective liquid product is added to a 10 milliliter volumetric flask. Then the contents of the flask are diluted with dichloromethane by adding dichloromethane up to the 10 milliliter mark. The resulting contents of the flask are referred to as the sample solution.

Fourth, a resultant solution is prepared in the following manner. A weight of 0.05 g of an aliquot portion of the selective liquid product is added to a 10 milliliter volumetric flask. The spiking solution is then added to the flask up to the 10 milliliter mark to dilute the contents. The resulting contents of the flask are referred to as the resultant solution.

Both the sample solution and the resultant solution are analyzed by GC/MS using the above-described conditions. Table 7 lists the ions that were extracted from the full MS scan, plotted, and integrated using the HP Chemstation software. The HP Chemstation software is used to determine the individual extracted ion peak areas that correspond to the internal quats listed in Table 7.

TABLE 7

Ratio of Mass to Charge of Ion for Peaks of Extracted Ions

| Internal Quaternary Phenyl-Alkane | Number of Carbon Atoms in Aliphatic Alkyl Group of the Internal Quaternary Phenyl-Alkane | Ratio of Mass to Charge (m/z) of Two Extracted Ions Corresponding to Internal Quaternary Phenyl-Alkane |
|---|---|---|
| 3-methyl-3-phenyl | 11 | 133 and 203 |
|  | 12 | 133 and 217 |
|  | 13 | 133 and 231 |
| 4-methyl-4-phenyl | 11 | 147 and 189 |
|  | 12 | 147 and 203 |
|  | 13 | 147 and 217 |
| 5-methyl-5-phenyl | 11 | 161 and 175 |
|  | 12 | 161 and 189 |
|  | 13 | 161 and 203 |

The concentration of each internal quaternary phenyl-alkane in Table 7 is computed using the following formula:

$$C = S\left(\frac{A_1}{A_2 - A_1}\right)$$

where
C=concentration of internal quaternary phenyl-alkane in sample solution, wt-%
S=concentration of internal quaternary phenyl-alkane in spiking solution, wt-%

A₁=peak area of internal quaternary phenyl-alkane in sample solution, area units A₂=peak area of internal quaternary phenyl-alkane in resultant solution, area units The concentrations C and S have the same units, provided that the areas A₁ and A₂ have the same units. Then, the concentration of each internal quaternary phenyl-alkane in the selective liquid product is computed from the concentration of that internal quaternary phenyl-alkane in the sample solution by accounting for the dilution effect of the dichloromethane in the sample solution. In this manner, the concentration in the selective liquid product of each of the internal quaternary phenyl-alkanes in Table 7 is computed. The total concentration of internal quaternary phenyl-alkanes in the selective liquid product, $C_{IQPA}$, is computed by summing the individual concentrations of each of the internal quaternary phenyl-alkanes in Table 7.

It should be pointed out that the selective liquid product may contain internal quaternary phenyl-alkanes other than those listed in Table 7, such as m-methyl-m-phenyl-alkanes where m>5, depending on the number of carbon atoms in the aliphatic alkyl groups of the phenyl-alkanes. It is believed that, with the $C_{12}$ olefinic stream and the conditions of this example, the concentrations of such other internal quaternary phenyl-alkanes are relatively low compared to those of the internal quaternary phenyl-alkanes listed in Table 7. Therefore, for purposes of this example, the total concentration of internal quaternary phenyl-alkanes in the selective liquid product, $C_{IQPA}$, is computed by summing only the individual concentrations of each of the internal quaternary phenyl-alkanes in Table 7. However, if the olefinic stream had comprised olefins having, say, up to 28 carbon atoms, then the total concentration of internal quaternary phenyl-alkanes in the selective liquid product, $C_{IQPA}$, would be computed by summing individual concentrations of m-methyl-m-phenyl-alkanes, where m is from 3 to 13. In more general terms, if the olefinic stream contains olefins having x carbon atoms, then the total concentration of internal quaternary phenyl-alkanes in the selective liquid product, $C_{IQPA}$, is computed by summing individual concentrations of m-methyl-m-phenyl-alkanes where m is from 3 to x/2. A person of ordinary skill in the art of gas chromatography/mass spectrometry can, without undue experimentation, identify at least one peak with a ratio of mass to charge (m/z) of an extracted ion corresponding to each internal quaternary phenyl-alkane, so that the concentration of all internal quaternary phenyl-alkanes may be determined and then summed to arrive at $C_{IQPA}$.

The selectivity to internal quaternary phenyl-alkanes in the selective liquid product is computed using the following formula:

$$Q = 100\left(\frac{C_{IQPA}}{C_{MAB}}\right)$$

where

Q=selectivity to internal quaternary phenyl-alkanes $C_{IQPA}$=concentration of internal quaternary phenyl-alkanes in selective liquid product, wt-%

$C_{MAB}$=concentration of modified alkylbenzenes in selective liquid product, wt-%

The concentration of modified alkylbenzenes, $C_{MAB}$, in the selective liquid product is determined in the following manner. First, the concentration of impurities in the selective liquid product is determined by a gas chromatography method. As used in this context of determining $C_{MAB}$, the term "impurities" means components of the selective liquid product that lie outside a specific retention time range that is used in the gas chromatography method. "Impurities" generally includes benzene, some dialkylbenzenes, olefins, paraffins, etc.

To determine the amount of impurities from the selective liquid product, the following gas chromatography method is used. The scope of the invention as set forth in the claims is not limited to determining the amount of impurities by use of only the specific equipment, specific sample preparation, and specific GC parameters described below. Equivalent equipment, equivalent sample preparation, and equivalent GC parameters that are different but that produce equivalent results to those described below may also be used to determine the amount of impurities in the selective liquid product.

Equipment:
  Hewlett Packard Gas Chromatograph HP 5890 Series II equipped with a split/splitless injector and flame-ionization detector (FID)
  J&W Scientific capillary column DB-1 HT, 30 meter length, 0.25 mm inside diameter, 0.1 micro-meter film thickness, catalog no. 1221131.
  Restek Red lite Septa 11 mm, catalog no. 22306. (Available from Restek Corporation, 110 Benner Circle, Bellefonte, Pa., USA).
  Restek 4 mm Gooseneck inlet sleeve with a carbofrit, catalog no. 20799-209.5.
  O-ring for inlet liner Hewlett Packard, catalog no. 5180-4182.
  J. T. Baker HPLC grade methylene chloride, catalog no. 9315-33, or equivalent. (Available from J. T. Baker Co., 222 Red School Lane, Phillipsburg, N.J., USA).
  2 ml gas chromatograph autosampler vials with crimp tops, or equivalent.

Sample Preparation:
  Weigh 4-5 mg of sample into a 2 ml GC autosampler vial.
  Add 1 ml methylene chloride to the GC vial; seal with 11 mm crimp vial Teflon lined closures (caps), HP part no. 5181-1210 (available from Hewlett Packard Company), using crimper tool, HP part no. 8710-0979 (available from Hewlett Packard Company); and mix well.
  The sample is now ready for injection into the GC.

GC Parameters:
  Carrier gas: hydrogen.
  Column head pressure: 9 psi.
  Flows: column flow, 1 ml/min; split vent, about 3 ml/min; septum purge, 1 ml/min.
  Injection: HP 7673 Autosampler, 10 microliter syringe, 1 microliter injection.
  Injector temperature: 350° C. (662° F.)
  Detector temperature: 400° C. (752° F.)
  Oven temperature program: initial hold at 70° C. (158° F.) for 1 minute; heating rate of 1° C. per minute (1.8° F. per minute); final hold at 180° C. (356° F.) for 10 minutes.

Two standards that have been freshly distilled to a purity of more than 98 mol-% are required for this gas chromatography method. In general, each standard is a 2-phenyl-alkane. One of the 2-phenyl-alkane standards, which is referred to hereinafter as the light standard, has at least one fewer carbon atom in its aliphatic alkyl group than that of the olefin in the olefinic stream charged to the alkylation zone that has the fewest number of carbon atoms. The other 2-phenyl-alkane standard, which is referred to hereinafter as the heavy standard, has at least one more carbon atom in its aliphatic alkyl group than that of the olefin in the olefinic stream charged to the alkylation zone that has the most number of carbon atoms. For example, if the olefins in the olefinic stream that is charged to the alkylation zone have from 10 to 14 carbon atoms, then the suitable standards include 2-phenyl-octane as the light standard and 2-phenyl-pentadecane as the heavy standard.

Each standard is subjected to the gas chromatography method using the conditions specified above to determine its retention time, and the two standard retention times in turn define a retention time range. Then, an aliquot sample of the selective liquid product is analyzed by the gas chromatography method using the above conditions. If more than about 90% of the total GC area is within the retention time range, then the impurities in the selective liquid product are deemed to be not more than about 10 wt-% of the selective liquid product, and, for the sole purpose of computing the selectivity to internal quaternary phenyl-alkanes, $C_{MAB}$ is assumed to be 100 wt-%.

On the other hand, if the percent of the total GC area within the retention time range is not more than about 90%, then the impurities in the selective liquid product are deemed to be more than about 10 wt-% of the selective liquid product. In this case, in order to determine $C_{MAB}$, impurities are removed from the selective liquid product, and the following distillation method is used. However, the scope of the invention as set forth in the claims is not limited to removing impurities from the selective liquid product using only the specific equipment, specific sample preparation, and specific distillation conditions described below. Equivalent equipment, equivalent procedures, and equivalent distillation conditions that are different but that produce equivalent results to those described below may also be used to remove impurities in the selective liquid product.

The distillation method to remove impurities from the selective liquid product is as follows. A 5-liter, 3-necked round bottom flask with 24/40 joints is equipped with a magnetic stir bar. A few boiling chips are added to the flask. A 9½ inch (24.1 cm) long Vigreux condenser with a 24/40 joint is placed in the center neck of the flask. A water cooled condenser is attached to the top of the Vigreux condenser which is fitted with a calibrated thermometer. A vacuum receiving flask is attached to the end of the condenser. A glass stopper is placed in one side arm of the 5-liter flask and a calibrated thermometer is placed in the other side arm. The flask and the Vigreux condenser are wrapped with aluminum foil. To the 5-liter flask is added a weight of 2200 to 2300 g of an aliquot portion of the selective liquid product which contains about 10 wt-% or more of impurities, as determined by the above gas chromatography method. A vacuum line leading from a vacuum pump is attached to the receiving flask. The selective liquid product in the 5-liter flask is stirred, and vacuum is applied to the system. Once the maximum vacuum is reached (at least 1 inch (25.4 mm) Hg by gauge or less), the selective liquid product is heated by means of an electric heating mantle.

After the heating begins, the distillate is collected in two fractions. One fraction, which is referred to hereinafter as fraction A, is collected from about 25° C. (77° F.) to about the temperature of the boiling point of the light standard at the pressure at the top of the Vigreux condenser, as measured by the calibrated thermometer at the top of the Vigreux condenser. The other fraction, fraction B, is collected from about the temperature of the boiling point of the light standard at the pressure at the top of the Vigreux condenser to about the temperature of the boiling point of the heavy standard at the pressure at the top of the Vigreux condenser, as measured by the calibrated thermometer at the top of the Vigreux condenser. Low-boiling fraction A and high-boiling pot residues are discarded. Fraction B contains the modified alkylbenzenes of interest, and is weighed. A person of ordinary skill in the art of distillation can scale this method as needed. Vapor pressures for phenyl-alkanes at various temperatures can be determined from the article written by Samuel B. Lippincott and Margaret M. Lyman, published in Industrial and Engineering Chemistry, Vol. 38, in 1946, and starting at page 320. Using the Lippincott et al. article and without undue experimentation, a person of ordinary skill in the art can determine appropriate temperatures for collecting fractions A and B.

Next, an aliquot sample of fraction B is analyzed by the gas chromatography method using the above conditions. If more than about 90% of the total GC area for fraction B is within the retention time range, then the impurities in fraction B are deemed to be not more than about 10 wt-% of the selective liquid product, and, for the sole purpose of computing the selectivity to internal quaternary phenyl-alkanes, $C_{MAB}$ is computed by dividing the weight of fraction B collected by the weight of the aliquot portion of the selective liquid product charged to the 5-liter flask in the above distillation method. On the other hand, if the percent of the total GC area for fraction B within the retention time range is not more than about 90%, then the impurities in fraction B are deemed to be more than about 10 wt-% of fraction B. In this case, impurities are removed from fraction B by again using the above distillation method. Accordingly, a low-boiling fraction (which is referred to as fraction C), high-boiling pot residues are discarded, a fraction (which is referred to herein as fraction D) containing the modified alkylbenzenes of interest is recovered and weighed, and an aliquot sample of fraction D is analyzed by the gas chromatography method. If more than about 90% of the total GC area for fraction D is within the retention time range, then for the sole purpose of computing the selectivity to internal quaternary phenyl-alkanes, $C_{MAB}$ is computed by dividing the weight of fraction D by the weight of the aliquot portion of the selective liquid product originally charged to the 5-liter flask. Otherwise, the distillation and gas chromatography methods are repeated for fraction D.

A person of ordinary skill in the art of distillation and gas chromatography will appreciate that the above-described distillation and gas chromatography methods can be repeated until a fraction containing the modified alkylbenzenes of interest and having less than 10 wt-% impurities is collected, provided that sufficient quantity of material remains after each distillation for further testing by these methods. Then, once $C_{MAB}$ is determined, the selectivity to internal quaternary phenyl-alkanes, Q, is computed using the above formula.

The results of these analyses are shown in the Table 8:

TABLE 8

Liquid Product Analysis

| 2-Phenyl-Alkane Selectivity | End Quaternary Phenyl-Alkane Selectivity | Internal Quaternary Phenyl-Alkane Selectivity |
|---|---|---|
| 82.0% | 6.98% | 1.9% |

In the absence of shape selectivity, such as if an alkylation catalyst such as aluminum chloride or HF were used, most of the 2-methyl undecene would be expected to form 2-methyl-2-phenyl undecane (that is, an end quat). Likewise, most of the 6-methyl undecene, 5-methyl undecene, 4-methyl undecene, and 3-methyl undecene would be expected to form internal quats. The linear olefins would be expected to produce a statistical distribution of 2-phenyl-dodecane, 3-phenyl-dodecane, 4-phenyl-dodecane, 5-phenyl-dodecane, and 6-phenyl-dodecane. Thus, if the lights, the heavies, and the other alkyl olefins listed in Table 5 are excluded from the computations, the 2-phenyl-alkane selectivity would be no greater than 17 and the internal quaternary phenyl-alkane selectivity would approach 55. Table 8 shows that the 2-phenyl-alkane selectivity is significantly higher than expected in the absence of shape selectivity and that the internal quaternary alkylbenzene selectivity obtained using the mordenite catalyst is much less than the internal quaternary alkylbenzene selectivity that would be expected in the absence of shape selectivity.

What is claimed is:

1. A modified alkylbenzene composition produced by a process, the process comprising the steps of:
    a) passing a feed stream comprising a lightly branched $C_{10}$-$C_{28}$ acyclic paraffin and at least one other acyclic paraffin and having a first concentration of the lightly branched acyclic paraffin to an adsorption zone comprising a bed of an absorbent comprising silicalite at adsorption promoting conditions to selectively adsorb the lightly branched acyclic paraffin, contacting the bed of adsorbent with a desorbent stream comprising at least one component selected from the group consisting of a $C_5$-$C_8$ cycloparaffin, a $C_5$-$C_8$ normal paraffin, and a $C_5$-$C_8$ branched paraffin and recovering from the adsorption zone an adsorption extract having a second concentration of the lightly branched acyclic paraffin that is greater than the first concentration;
    b) passing at least a portion of the adsorption extract to a dehydrogenation zone, operating the dehydrogenation zone at dehydrogenation conditions sufficient to dehydrogenate the acyclic paraffin, and recovering from the dehydrogenation zone a dehydrogenated product stream comprising a lightly branched $C_{10}$-$C_{28}$ acyclic monoolefin;
    c) passing a feedstock comprising a phenyl compound and passing at least a portion of the dehydrogenated product stream comprising the acyclic lightly branched monoolefin to an alkylation zone, operating the alkylation zone at alkylation conditions sufficient to alkylate the phenyl compound with the lightly branched acyclic monoolefin in the presence of a solid, molecular sieve alkylation catalyst to form phenyl-alkanes comprising molecules having one phenyl portion and one $C_{10}$-$C_{28}$ aliphatic alkyl portion; wherein the aliphatic alkyl portion has no quaternary carbon atoms except for any quaternary carbon atom bonded by a carbon-carbon bond with a carbon atom of the phenyl portion; and wherein the phenyl-alkanes have selectivity to 2-phenyl-alkanes of from about 40 to about 100 and a selectivity to internal quaternary phenyl-alkanes of less than 10; and
    d) recovering the phenyl-alkanes from the alkylation zone.

2. The composition of claim 1 wherein the phenyl-alkanes have a selectivity to 2-phenyl-alkanes of from about 50 to about 100.

3. The composition of claim 1 wherein the phenyl-alkanes have a selectivity to 2-phenyl-alkanes of about 60 to about 100.

4. The composition of claim 1 wherein the phenyl-alkanes have a selectivity to internal quaternary phenyl-alkanes of less than about 8.

5. The composition of claim 1 wherein the phenyl-alkanes have a selectivity to internal quaternary phenyl-alkanes of less than 5.

6. The composition of claim 1 further characterized in that the phenyl-alkanes have a selectivity to phenyl-alkanes having an aliphatic alkyl portion containing a quaternary carbon atom not bonded by a carbon-carbon bond with a carbon atom of the phenyl portion of less than 1.

7. The composition of claim 1 further characterized in that the feed stream has a concentration of the lightly branched paraffin of more than about 30 mol-%.

8. The composition of claim 1 further characterized in that the process comprises simulating the use of a moving bed of adsorbent.

9. The composition of claim 1 further characterized in that the lightly branched acyclic paraffin comprises a monomethyl paraffin.

10. The composition of claim 1 further characterized in that the desorbent stream comprises a compound selected from the group consisting of normal pentane, normal hexane, methylcyclohexane, a cyclopentane, and isooctane.

11. The composition of claim 1 further characterized in that the alkylation catalyst comprises a zeolite having a zeolite structure type selected from the group consisting of BEA, MOR, MTW, and NES.

12. The composition of claim 1 further characterized in that the absorption extract steam has a concentration of the normal paraffin of less than about 75 mol-%.

13. The composition of claim 1 further characterized in that the lightly branched acyclic comprises a lightly branched olefin having 3 primary carbon atoms and that the at least a portion of the dehydrogenated product stream has a concentration of the lightly branched olefin of more than 85 mol-%, based on the total lightly branched olefins in the at least a portion of the dehydrogenated product stream.

14. The composition of claim 1 further characterized in that a makeup stream comprising nonbranched paraffins passes to the dehydrogenation zone.

15. The composition of claim 1 further characterized in that the feed stream has a concentration of the normal paraffin of more than 0.3 mol-%.

16. A modified alkylbenzene sulfonate composition produced by a process, the process comprising the steps of:
    a) passing a feed stream comprising a lightly branched $C_{10}$-$C_{28}$ acyclic paraffin and at least one other acyclic paraffin and having a first concentration of the lightly branched acyclic paraffin to an adsorption zone comprising a bed of an adsorbent comprising silicalite at adsorption promoting conditions to selectively adsorb the lightly branched acyclic paraffin, contacting the bed of adsorbent with a desorbent stream comprising at least one component selected from the group consisting of a $C_5$-$C_8$ cycloparaffin, a $C_5$-$C_8$ normal paraffin, and a $C_5$-$C_8$ branched paraffin and recovering from the adsorption zone an adsorption extract having a second concentration of the lightly branched acyclic paraffin that is greater than the first concentration;
    b) passing at least a portion of the adsorption extract to a dehydrogenation zone, operating the dehydrogenation zone at dehydrogenation conditions sufficient to dehydrogenate the lightly branched acyclic paraffin, and recovering from the dehydrogenation zone a dehydrogenated product steam comprising a lightly branched $C_{10}$-$C_{28}$ acyclic monoolefin;
    c) passing a feedstock comprising a phenyl compound and passing at least a portion of the dehydrogenated product stream comprising the lightly branched acyclic monoolefin, to an alkylation zone, operating the alkylation zone at alkylation conditions sufficient to alkylate the phenyl compound with the lightly branched acyclic monoolefin in the presence of a solid, molecular sieve alkylation catalyst to form phenyl-alkanes comprising molecules having one phenyl portion and one $C_{10}$-$C_{28}$ aliphatic alkyl portion; wherein the aliphatic alkyl portion has no quaternary carbon atoms except for any quaternary carbon atom bonded by a carbon-carbon bond with a carbon atom of the phenyl portion; and wherein the phenyl-alkanes have a selectivity to 2-phenyl-alkanes of from about 40 to about 100 and a selectivity to internal quaternary phenyl-alkanes of less than 10;

d) withdrawing an alkylate product stream comprising the phenylalkanes from the alkylation zone and contacting at least a portion of the alkylate product stream with a sulfonating agent at sulfonation conditions sufficient to sulfonate phenyl-alkanes and to produce a sulfonated product stream comprising phenyl-alkane sulfonic acids; and e) contacting at least a portion of the sulfonated product stream with a neutralizing agent at neutralization conditions sufficient to neutralize phenyl-alkane sulfonic acids and to produce phenyl-alkane sulfonates.

17. A modified alkylbenzene composition produced by a process, the process comprising the steps of:

a) passing a feed stream comprising a desired monomethyl paraffin and a raffinate compound to a bed of an adsorbent comprising silicalite, wherein the adsorbent selectively retains the monomethyl paraffin comprising $C_{10}$-$C_{28}$ acyclic paraffins, wherein the bed is located in a continuous simulated moving bed adsorptive separation zone comprising an adsorbent chamber containing a number of compartmentalized beds of the adsorbent, and wherein the compartmentalized beds are separated by transfer points for streams used in the process, and withdrawing a raffinate stream comprising the raffinate compound from the adsorbent chamber;

b) passing a desorbent stream comprising at least one desorbent selected from the group consisting of a $C_5$-$C_8$ cycloparaffin, a $C_5$-$C_8$ normal paraffin, and a $C_5$-$C_8$ branched paraffin, to the adsorbent chamber, and removing an extract stream comprising the desorbent and the desired monomethyl paraffin from the adsorbent chamber;

c) periodically incrementing the transfer points in the adsorbent chamber of the feed, desorbent, extract, and raffinate streams to simulate countercurrent movement of the beds of adsorbent and the feed stream;

d) passing at least a portion of the extract stream to a dehydrogenation zone, operating the dehydrogenation zone at dehydrogenation condition sufficient to dehydrogenate the monomethyl paraffin, and recovering from the dehydrogenation zone a dehydrogenated product stream comprising a monomethyl monoolefin;

e) passing a feedstock comprising benzene and passing at least a portion of the dehydrogenated product stream comprising the monomethyl monoolefin to an alkylation zone, operating the alkylation zone at alkylation conditions sufficient to alkylate benzene with the monomethyl monoolefin in the presence of a solid, molecular sieve alkylation catalyst to form phenyl-alkanes comprising molecules having one phenyl portion and one aliphatic alkyl portion;

wherein the aliphatic alkyl portion has 2 or 3 primary carbon atoms and no quaternary carbon atoms except for any quaternary carbon atom bonded by a carbon-carbon bond with a carbon atom of the phenyl portion; and wherein the phenyl-alkanes have a selectivity to 2-phenyl-alkanes of from about 40 to about 100 and a selectivity to internal quaternary phenyl-alkanes of less than 10 and a selectivity to phenyl-alkanes having an aliphatic alkyl portion containing a quaternary carbon atom not bonded by a carbon-carbon bond with a carbon atom of the phenyl portion of less than 1; and f) recovering the phenyl-alkanes from the alkylation zone.

18. The composition of claim 17 wherein the phenyl-alkanes have a selectively to 2-phenyl alkanes of from about 50 to about 100.

19. The composition of claim 17 wherein the phenyl-alkanes have a selectively to 2-phenyl alkanes of from about 60 to about 100.

20. The composition of claim 17 wherein the phenyl-alkanes have a selectivity to internal quaternary phenyl-alkanes of less than 5.

21. A modified alkylbenzene composition produced by a process comprising the steps of:

a) providing a feed stream comprising a feed mixture comprising aromatic hydrocarbons;

b) enriching the first feed stream for lightly branched paraffins to produce a second feed stream comprising $C_{10}$-$C_{28}$ acyclic paraffins, wherein the second feed stream contains a higher concentration of lightly branched paraffins based on the total paraffins in the second feed stream, than the concentration of lightly branched paraffins in the feed mixture based on the total concentration of paraffins in the feed mixture;

c) dehydrogenating components of the second feed stream to produce a dehydrogenated product stream comprising lightly branched monoolefins;

d) passing a feedstock comprising a phenyl compound and passing at least a portion of the dehydrogenated product stream to an alkylation zone under conditions, using a solid, molecular sieve alkylation catalyst, sufficient to alkylate the phenyl compound with the lightly branched monoolefin and form an alkylate product stream comprising phenyl alkanes;

e) contacting at least a portion of the alkylate product stream with a sulfonating agent under conditions sufficient to sulfonate phenyl alkanes and produce phenyl-alkane sulfonic acids; and f) neutralizing the phenyl-alkane sulfonic acids and to produce phenyl-alkane sulfonates, wherein the aliphatic alkyl portion of the phenyl-alkane sulfonic acid have no quaternary carbon atoms except for any quaternary carbon atom bonded by a carbon-carbon bond with a carbon atom of the phenyl portion, and wherein the phenyl-alkanes have selectivity to 2-phenyl-alkanes of from about 40 to about 100 and a selectivity to internal quaternary phenyl-alkanes of less than 10.

22. The composition of claim 21, wherein the first feed stream is enriched for lightly branched paraffins by contacting the first feed stream with an adsorption zone comprising a bed of an absorbent comprising silicalite at adsorption promoting conditions to selectively adsorb the lightly branched paraffins.

23. The composition of claim 21, wherein the feed mixture has a concentration of the lightly branched paraffin of more than about 30 mol-%.

* * * * *

UNITED STATES PATENT AND TRADEMARK OFFICE
CERTIFICATE OF CORRECTION

PATENT NO. : 7,795,483 B2  
APPLICATION NO. : 10/658703  
DATED : September 14, 2010  
INVENTOR(S) : Kulprathipanja et al.

It is certified that error appears in the above-identified patent and that said Letters Patent is hereby corrected as shown below:

Column 44,  
Claim 18.  
Line 12, replace "have a selectively to 2-phenyl alkanes" with --have a selectivity to 2-phenyl alkanes--

Column 44,  
Claim 19.  
Line 15, replace "have a selectively to 2-phenyl alkanes" with --have a selectivity to 2-phenyl alkanes--

Signed and Sealed this

Sixteenth Day of November, 2010

David J. Kappos  
*Director of the United States Patent and Trademark Office*